(12) United States Patent
Eisenstein et al.

(10) Patent No.: US 9,855,225 B2
(45) Date of Patent: Jan. 2, 2018

(54) CANNABINOID RECEPTOR TREATMENTS

(75) Inventors: Toby K. Eisenstein, Wyndmoor, PA (US); Rebecca R. Hartzell, Indian Rocks Beach, FL (US); Martin W. Alder, Warrington, PA (US); Joseph J. Meissier, Ardmore, PA (US)

(73) Assignee: TEMPLE UNIVERSITY OFFICE OF TECHNOLOGY TRANSFER, Philadelphia, PA (US)

( * ) Notice: Subject to any disclaimer, the term of this patent is extended or adjusted under 35 U.S.C. 154(b) by 101 days.

(21) Appl. No.: 14/239,413

(22) PCT Filed: Aug. 17, 2012

(86) PCT No.: PCT/US2012/051330
§ 371 (c)(1),
(2), (4) Date: Feb. 26, 2016

(87) PCT Pub. No.: WO2013/025984
PCT Pub. Date: Feb. 21, 2013

(65) Prior Publication Data
US 2017/0014355 A1    Jan. 19, 2017

Related U.S. Application Data

(60) Provisional application No. 61/524,883, filed on Aug. 18, 2011.

(51) Int. Cl.
| | | |
|---|---|---|
| *A61K 31/09* | (2006.01) |
| *A61K 31/095* | (2006.01) |
| *A61K 31/35* | (2006.01) |
| *A61K 31/352* | (2006.01) |
| *A61K 31/404* | (2006.01) |
| *A61K 31/415* | (2006.01) |
| *A61K 31/454* | (2006.01) |
| *A61K 39/395* | (2006.01) |
| *A61K 45/06* | (2006.01) |
| *C07K 16/24* | (2006.01) |

(52) U.S. Cl.
CPC ............ *A61K 31/09* (2013.01); *A61K 31/095* (2013.01); *A61K 31/35* (2013.01); *A61K 31/352* (2013.01); *A61K 31/404* (2013.01); *A61K 31/415* (2013.01); *A61K 31/454* (2013.01); *A61K 39/3955* (2013.01); *A61K 45/06* (2013.01); *C07K 16/244* (2013.01)

(58) Field of Classification Search
CPC ............................. A61K 31/09; A61K 31/095
See application file for complete search history.

(56) References Cited

U.S. PATENT DOCUMENTS

| | | | | |
|---|---|---|---|---|
| 2005/0159449 A1* | 7/2005 | Martin | ................ | C07D 303/10 514/317 |
| 2008/0139635 A1* | 6/2008 | Martin | ................ | A61K 31/045 514/397 |

* cited by examiner

*Primary Examiner* — Yong Chong
(74) *Attorney, Agent, or Firm* — Duane Morris LLP

(57) ABSTRACT

The present invention includes methods and compositions for treating a transplant recipient by administration of a $CB_2$ receptor agonist either alone or in combination with one or more active pharmaceutical ingredients to block the rejection of foreign tissue and prolong grafted organs, tissues and cells.

6 Claims, 16 Drawing Sheets

FIGURE 3A
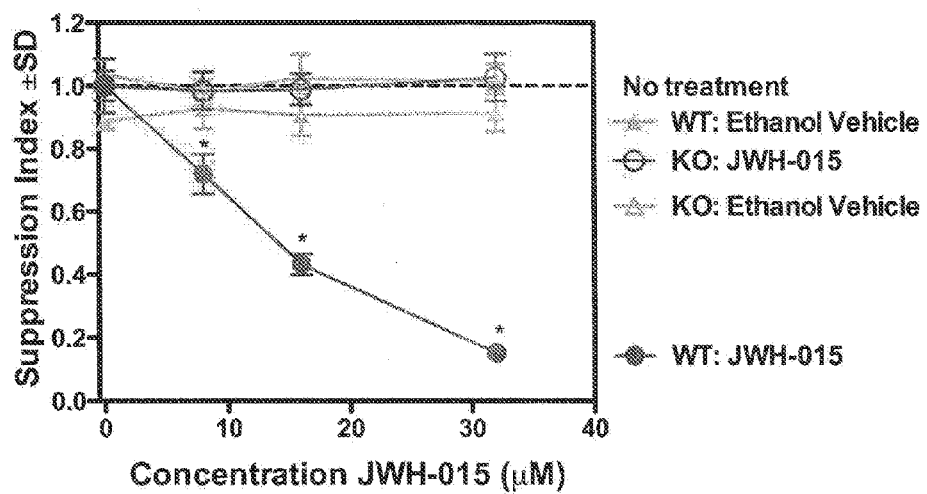
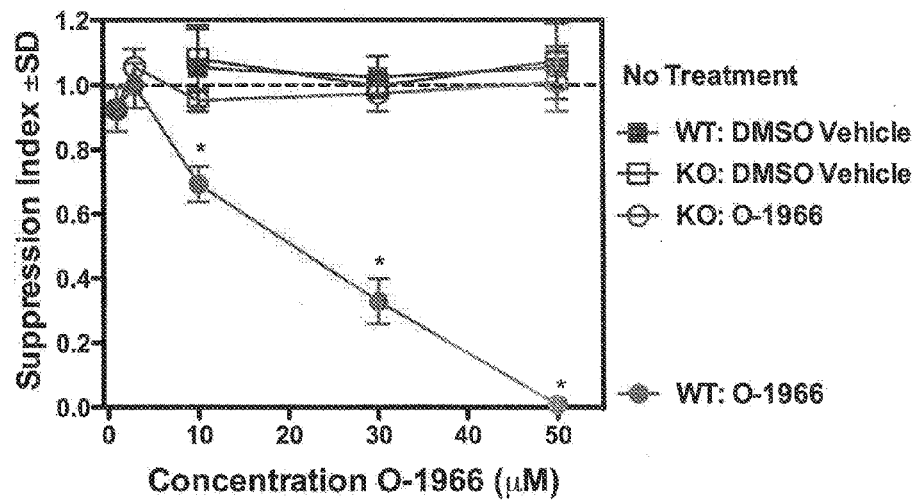
FIGURE 3B

CANNABINOID RECEPTOR TREATMENTS

CROSS-REFERENCE TO RELATED APPLICATIONS

This application is a U.S. national phase application filed under 35 U.S.C. §371 of International Application No.: PCT/US2012/051330, which was filed Aug. 17, 2012, and which claims the benefit of the filing date of U.S. Provisional Application No. 61/524,883, which was filed on Aug. 18, 2011. For the purpose of any U.S. application that may claim the benefit of U.S. Provisional Application No. 61/524,883, the contents of that earlier filed application are hereby incorporated by reference in their entirety.

U.S. GOVERNMENT RIGHTS

This invention was supported in part by United States Government Grant No. DA13429, DA06650 and T32-DA07237 awarded by National Institutes of Drug Abuse. The United States Government may have certain rights in the invention.

BACKGROUND

*Cannabis* and its derivatives have long been used for medicinal purposes. The major active ingredient of *cannabis*, also known as marijuana, is $\Delta^9$-tetrahydrocannabinol (THC). Studies on the effects of THC has led to the discovery of an endogenous system of ligands that are involved in many physiological actions including immune system responses in humans. Two cloned cannabinoid receptors have been identified, $CB_1$ and $CB_2$. The $CB_1$ receptor is expressed primarily on neurons in the brain but is also found to a lesser degree in peripheral tissues such as the vasculature and immune cells. Although the $CB_2$ receptor is found in the brain, it is found primarily on cells and tissues of the immune system including, spleen, thymus and tonsils. Activation of $CB_2$ receptors has been shown to modulate the immune system.

Cannabinoids, acting at $CB_2$ receptors, likely exert their immunosuppressive effects by one or more of several ways, including, but not limited to: 1) inducing apoptosis or programmed cell death in immune cells, 2) inhibiting cell proliferation, 3) inhibiting cytokine and chemokine production and 4) inducing regulatory T cells. The apoptotic properties of THC on immune cells has been well studied. For instance, in vivo administration of THC, an agonist at $CB_1$ and $CB_2$ receptors, leads to significant cell death of T cells, B cells, dendritic cells and macrophages in disease models using mice (McKallip R J, Lombard C, Martin B R, Nagarkatti M, Nagarkatti P S. (2002) Delta(9)-tetrahydrocannabinol-induced apoptosis in the thymus and spleen as a mechanism of immunosuppression in vitro and in vivo. *J Pharmacol Exp Ther* 302(2):451-65). However, the inventors have demonstrated that both THC and anandamide, an endogenous cannabinoid, induce dose-related immunosuppression in both the primary and secondary in vitro plaque-formation cell assays of antibody formation, a result that is not due to apoptosis. Pretreatment with a selective $CB_2$ receptor antagonist blocks immunosuppression in mouse splenocytes while pretreatment with a selective $CB_1$ receptor antagonist potentiated the in vitro effect at certain doses, suggesting that THC and anandamide mediate immune function effects through the $CB_2$ receptor. In addition, these results demonstrate that both exogenous and endogenous cannabinoids exert their effect on the immune system through $CB_2$ receptors.

It has been shown that broad spectrum cannabinoid agonists have potential as therapeutic agents, however, their medicinal use may be limited because of use and abuse. For example, one of the drawbacks of using marijuana, a $CB_1$/$CB_2$ receptor agonist, is the resulting psychotropic effects due to $CB_1$ receptor activation. Cannabinoids that selectively target $CB_2$ receptors, and thus, the immune system, have great clinical potential as therapeutic agents in the treatment of graft rejection since they are expected to have little or no $CB_1$ receptor activity (i.e. psychotropic effects).

Current immunosuppressant therapies used to prevent or block tissue rejection in organ transplantation are associated with significant untoward effects. For example, toxicity with chronic tacrolimus use is associated with post-transplantation diabetes mellitus (PTDM) due to the death of pancreatic islet cells, and also with kidney damage. Tacrolimus and rapamycin use may induce hyperkalemia. In addition, rapamycin may cause encephalopathies and other central nervous systems deficits including tremors and headache, as well as hypertension and hirsutism. Thus, there is an unmet need for definitive novel methods and/or therapies for blocking graft rejection in humans.

SUMMARY OF THE INVENTION

The present invention includes methods and compositions for treating a transplant recipient by administration of a $CB_2$ receptor agonist either alone or in combination with one or more active pharmaceutical ingredients to block the rejection of foreign tissue and prolong grafted organs, tissues and cells. In some embodiments, the methods include methods of reducing the likelihood of graft rejection in a patient in need thereof comprising the administration of a therapeutically effective amount of either a selective $CB_2$ receptor agonist or $CB_1$/$CB_2$ receptor agonist. The methods can further include administration of a therapeutically effective amount of a $CB_1$ receptor antagonist, and in some embodiments, administration of a therapeutically effective amount of an immunosuppressive agent.

BRIEF DESCRIPTION OF THE FIGURES

FIGS. 3A and 3B are graphs showing that the selective $CB_2$ receptor agonists, JWH-015 and O-1966, inhibited the mixed lymphocyte reaction in splenocytes from wildtype (WT) mice, but not mice missing the $CB_2$ receptor ($CB_2R^{(-/-)}$ knockout (KO) mice).

DETAILED DESCRIPTION OF THE INVENTION

Figure 1A:
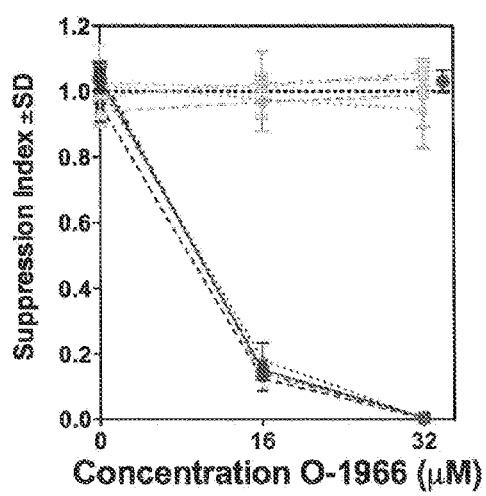
FIGS. 1A and 1B are graphs showing that a selective $CB_2$ receptor antagonist (SR144528), but not a selective $CB_1$ receptor antagonist (SR141716A), blocked suppression of the mixed lymphocyte reaction by the selective $CB_2$ agonists JWH-015 and O-1966.

The present invention features methods of reducing the likelihood of graft rejection in a patient. The methods can include a step of administering to the patient a therapeutically effective amount of a composition, e.g., a pharmaceutical composition, that targets cannabinoid receptors. The compositions can include one or more selective $CB_2$ receptor agonists, or one or more $CB_1/CB_2$ receptor agonists, or a combination of one or more selective $CB_2$ receptor agonists and a combination of one or more $CB_1/CB_2$ receptor agonists. In some embodiments, the compositions can include one or more $CB_1$ receptor antagonists and or one or more immunosuppressive agents.

The graft can be an allograft or xenograft and can be of an organ, such as a heart, kidney, liver or a lobe thereof, lung or a lobe thereof, pancreas or a portion thereof, bone marrow, cartilage, skin, a cornea, neuronal tissue, or muscle. The graft can also include a population of cells that do not define an intact organ. Transplanted cells can also include stem cells (e.g., mesenchymal stem cells, adult stem cells, or fetal stem cells).

Thus, embodiments of the invention are directed to methods and compositions used for blocking or preventing rejection of foreign tissue in a transplant recipient that is responsive to $CB_2$ receptor activation. The types of foreign tissue targeted include organ and skin transplants as well as the transplant of foreign cells such as bone marrow cells, stem cells or other purified cell populations. The method includes, for example, administering a therapeutically effective amount of: 1) a selective $CB_2$ receptor agonist administered either alone, or in combination with an immunosuppressive agent, 2) a selective $CB_2$ receptor agonist administered in combination with an immunosuppressive agent, and a $CB_1$ receptor antagonist, 3) a selective $CB_2$ receptor agonist administered in combination with a $CB_1$ receptor antagonist, 4) a $CB_1/CB_2$ receptor agonist administered either alone, or in combination with an immunosuppressive agent, 5) a $CB_1/CB_2$ receptor agonist administered with a $CB_1$ receptor antagonist and an immunosuppressive agent, and 6) a $CB_1/CB_2$ receptor agonist administered with a $CB_1$ receptor antagonist.

The compositions disclosed herein can include, for example: 1) selective $CB_2$ receptor agonists either alone, or combined with an immunosuppressive agent, 2) selective $CB_2$ receptor agonists combined with an immunosuppressive agent, and a $CB_1$ receptor antagonist, 3) selective $CB_2$ receptor agonists combined with a $CB_1$ receptor antagonist, 4) $CB_1/CB_2$ receptor agonists either alone, or combined with an immunosuppressive agent, 5) $CB_1/CB_2$ receptor agonists combined with an immunosuppressive agent, and a $CB_1$ receptor antagonist, and 6) $CB_1/CB_2$ receptor agonists combined with a $CB_1$ receptor antagonist. Any of the compositions can be formulated as pharmaceutical compositions. Any of the pharmaceutical compositions of the invention can be formulated for use in the preparation of a medicament, and particular uses are indicated below in the context of treatment.

In one embodiment, a method is provided for administering a therapeutically effective amount of a selective $CB_2$ receptor agonist to block or prevent rejection of foreign tissue in a transplant recipient.

In another embodiment, a method is provided for administering a therapeutically effective amount of a selective $CB_2$ receptor agonist and an immunosuppressive agent to block or prevent rejection of foreign tissue in a transplant recipient.

In another embodiment, a method is provided for administering a therapeutically effective amount of a selective $CB_2$ receptor agonist, and a $CB_1$ receptor antagonist to block or prevent rejection of foreign tissue in a transplant recipient.

In another embodiment, a method is provided for administering a therapeutically effective amount of a selective $CB_2$ receptor agonist, an immunosuppressive agent and $CB_1$ receptor antagonist to block or prevent rejection of foreign tissue in a transplant recipient.

Still another embodiment includes a method for administering a therapeutically effective amount of a $CB_1/CB_2$ receptor agonist to block or prevent rejection of foreign tissue in a transplant recipient.

Another embodiment provides a method of administering a therapeutically effective amount of a $CB_1/CB_2$ receptor agonist and an immunosuppressive agent to block or prevent rejection of foreign tissue in a transplant recipient.

Another embodiment includes a method for administering a therapeutically effective amount of a $CB_1/CB_2$ receptor agonist and a $CB_1$ receptor antagonist to block or prevent rejection of foreign tissue in a transplant recipient.

Yet another embodiment provides a method of administering a therapeutically effective amount of a $CB_1/CB_2$ receptor agonist, a $CB_1$ receptor antagonist, and an immunosuppressive agent to block or prevent rejection of foreign tissue in a transplant recipient.

The invention is also directed to pharmaceutical compositions comprising one or more active pharmaceutical ingredients which includes a $CB_2$ receptor agonist along with one or more pharmaceutically acceptable excipients, diluents or carriers, wherein the composition is administered to block or prevent tissue rejection.

In one embodiment, the invention includes a pharmaceutical composition wherein the active pharmaceutical ingredient is one or more selective $CB_2$ receptor agonists.

Another embodiment includes a pharmaceutical composition wherein the active pharmaceutical ingredients comprise one or more selective $CB_2$ receptor agonists and an immunosuppressant agent.

Another embodiment includes a pharmaceutical composition wherein the active pharmaceutical ingredients comprise one or more selective $CB_2$ receptor agonists and an $CB_1$ receptor antagonist.

Yet another embodiment includes a pharmaceutical composition wherein the active pharmaceutical ingredients comprise one or more selective $CB_2$ receptor agonists, an immunosuppressant agent and a $CB_1$ receptor antagonist.

Still another embodiment includes a pharmaceutical composition wherein the active pharmaceutical ingredients comprise one or more $CB_1/CB_2$ receptor agonists.

Another aspect includes a pharmaceutical composition wherein the active pharmaceutical ingredients comprise one or more $CB_1/CB_2$ receptor agonists and an immunosuppressant agent.

Still another embodiment includes a pharmaceutical composition wherein the active pharmaceutical ingredients comprise one or more $CB_1/CB_2$ receptor agonists and a $CB_1$ receptor antagonist.

Yet another embodiment includes a pharmaceutical composition wherein the active pharmaceutical ingredients comprise one or more $CB_2$ receptor agonists, a $CB_1$ receptor antagonist and an immunosuppressant agent.

The combination therapies disclosed may be administered as one or more pharmaceutical compositions and, if separately, may be administered simultaneously or sequentially in any order.

Compositions

The compositions described herein include compounds that target cannabinoid receptors. The $CB_2$ receptor (also known as CB-2, CB2, CX5, hCB2, cannabinoid receptor 2 (macrophage), OTTHUMP00000015772, and OTTHUMP00000044841) is a 360 amino acid polypeptide encoded in humans by the CNR2 gene. The NCBI reference sequence for the human CB2 receptor can be found at GENBANK under accession number NP_001832.1, public GI:4502929. The $CB_1$ receptor (also known as CANN6, CB-R CB1, CB1A, CB1K5, CB1R, CNr, cannabinoid receptor 1, cannabinoid receptor 1 (brain), central cannabinoid receptor, OTTHUMP00000016838, OTTHUMP00000016839, and OTTHUMP00000016840) is a 472 amino acid polypeptide encoded in humans by the CNR1 gene. The NCBI reference sequence for the human $CB_1$ receptor can be found at GENBANK under accession number NP_001153698.1 public GI:237681067.

Cannabinoids are a group of compounds that specifically bind to and activate cannabinoid receptors. Cannabinoids include both phytocannabinoids, i.e., cannabinoids that are produced by plants of the genus *Cannabis*, and endocannabinoids, i.e., compounds produced by animal cells that act as endogenous ligands for cannabinoid receptors. Cannabinoids can be isolated from natural sources, for example, *Cannabis sativa* or human cells, or they can be chemically synthesized. Generally, cannabinoid compounds fall into five structural classes. The first class, the classical cannabinoids, are tricyclic-dibenzopyran derivatives isolated from the plant *Cannabis sativa*, and include Δ9-tetrahydrocannabinol (THC) or close synthetic analogues, such as HU-210. The second class, the non-classical cannabinoids, are structurally similar to the classical cannabinoids, but are AC-bicyclic and ACD-tricyclic analogues lacking the dihydropyran ring. The prototype for this class is CP-55940 (CP). The third class includes aminoalkylindoles, the prototypical compound being WIN55,212-2 (WIN). The fourth class encompasses derivatives of arachidonic acid, which are the endogenous ligands for cannabinoid receptors. Exemplary endocannabinoids include anandamide (arachidonoylethanolamide, AEA) and 2-arachidonoylglycerol (2-AG). The fifth class includes diarylpyrazole compounds, e.g., SR141716, (also known as rimonabant).

The compositions can include compounds from the structural classes above, but the invention is not so limited and can include compounds that do not fall within the structural classes above as long as those compounds retain sufficient biological activity to function (i.e., the ability to selectively bind to and activate the $CB_2$ receptor, or the ability to bind to and activate the $CB_1/CB_2$ receptor, or the ability to bind to and inactivate the $CB_1$ receptor) in the methods of the invention. Compositions suitable for use in the present methods include compounds that selectively bind to the $CB_2$ receptor and mimic action of a naturally-occurring ligand (for example, anandamide, 2-arachidonoylglycerol or THC), i.e., selective $CB_2$ receptor agonists and pharmaceutical compositions containing such compounds. Compositions suitable for use in the present methods also include compounds that bind to the $CB_1/CB_2$ receptor and mimic action of the naturally-occurring ligand, i.e., $CB_1/CB_2$ receptor agonists and pharmaceutical compositions containing such compounds. In some embodiments, the compositions can compounds that bind to the $CB_1$ receptor and blocks or dampens the ability of the naturally-occurring ligand to bind the receptor, i.e., $CB_1$ receptor antagonists and pharmaceutical compositions containing such compounds.

Although there are no universally accepted criteria, compounds are typically said to be selective for one receptor over another when their binding affinities are at least 100-fold different. Compounds are also defined as being agonists or antagonists according to their actions at the receptor. With respect to cannabinoid receptors, pure agonists generally mimic the effects of the naturally-occurring ligand; pure antagonists generally block the actions of an agonist while having no agonist activity of their own; and partial agonists can exhibit mixed actions, showing some degree of intrinsic positive activity at the receptor (albeit less than what would be seen with the naturally-occurring ligand) while also blocking the actions of an agonist under some conditions.

Compounds useful in the context of the present invention include pure and/or selective $CB_2$ receptor agonists, $CB_1/CB_2$ receptor agonists, pure and/or selective $CB_1$ receptor antagonists. Partial agonists and inverse agonists are also useful. Such compounds can be used alone or in any combination; in some embodiments, the compositions can include a mixture of two or more such compounds in equal or unequal amounts.

Selective $CB_2$ Receptor Agonist

The "cannabinoid receptor agonist" of the current invention can be a cannabinoid receptor 2 ($CB_2$) agonist. Expression of $CB_2$ receptors on immune cells and the findings that cannabinoids modulate immune responses show that $CB_2$ receptor agonists may be powerful therapeutic tools used for their immunosuppressive properties. Thus, in any of the methods described, the $CB_2$ receptor agonist can be selective for the $CB_2$ receptor. Specifically, a selective $CB_2$ receptor agonist is defined as having a binding affinity ratio at cannabinoid receptors (e.g. $CB_1$ Ki/$CB_2$ Ki) of at least 5. $CB_1$ and $CB_2$ receptors may be on the same cell or on different cells. Table 1 shows cannabinoid receptor binding affinities of several available $CB_2$ receptor agonists.

TABLE 1

Cannabinoid Receptor Binding Affinities

| CB Agent | CB1 (Ki, nM) | CB2 (Ki, nM) | CB1/CB2 Ratio |
|---|---|---|---|
| JWH-015 | 383 | 13.8 | 27.8 |
| O-1966 A | 5055 ± 984 | 23 ± 2.1 | 220 |
| O-1966 B | 1716 ± 105 | 111 ± 8 | 15 |
| THC (Marinol) | 39.5 | 40 | 1 |

The Ki's are listed as means ± SEM.

The selective $CB_2$ receptor agonist can include a resorcinol, a resorcinol derivative, a resorcinol analog or a combination thereof. Preferred selective $CB_2$ receptor agonists are dimethoxyresorcinol derivatives such as [(1R,2R,5R)-2-[2,6-dimethoxy-4-(2-methyloctan-2-yl)phenyl]-7,7-dimethyl-4-bicyclo[3.1.1]hept-3-enyl] methanol (HU-308); (6aR,10aR)-3-(1,1-Dimethylbutyl)-6a,7,10,10a-tetrahydro-6,6,9-trimethyl-6H-dibenzo[b,d]pyran (JWH-133); (6aR,10aR)-1-methoxy-6,6,9-trimethyl-3-(2-methyloctan-2-yl)-6a,7,10,10a-tetrahydrobenzo[c]chromene (L-759,633); PRS 211,375 (cannabinor); aminoalkylindole such as (3-iodo-5-nitrophenyl)-[1-[(1-methylpiperidin-2-yl)methyl]indol-3-yl]methanone (AM-1241), bicyclic resorcinols and their derivatives such as 2-(3-methylcyclohexyl)-5-(1,1'-dimethylheptyl)-resorcinol isomers (O-1797 and O-1798), 2-(3R-methylcyclohexyl)-5-(1,1'-dimethylheptyl)-resorcinol (O-1826); bicyclic hydroxyl resorcinol derivatives such as 1-{4-(1,1-Dimeyhyl-heptyl)-2,6-dimethoxy-phenyl}-3-methyl-cyclohexanol (O-2137 and its racemates O-1966, and O-1967); and 3,5 dihydroxyphenyl analogues of resorcinols such as O-3853; naphthoylindole cannabinoids such as 2-Methyl-1-propyl-1H-indol-3-yl)-1-naphthalenylmethanone (JWH-015); (6aR,10aR)-1-methoxy-6,6-dimethyl-9-methylidene-3-(2-methyloctan-2-yl)-7,8,10,10a-tetrahydro-6aH-benzo[c]chromene (L-759,656); benzofuran derivatives; 2-(2,4-dichloroanilino)-N-(tetrahydropyran-4-ylmethyl)-4-(trifluoromethyl)pyrimidine-5-carboxamide (GW-842,166X); N-(Piperidin-1-yl)-1-(2,4-dichlorophenyl)-1,4-dihydro-6-methylindeno[1,2-c]pyrazole-3-carboxamide (GP-1a). Selective $CB_2$ receptor agonists can include or exclude dimethoxyresorcinol derivatives such as [(1R,2R,5R)-2-[2,6-dimethoxy-4-(2-methyloctan-2-yl)phenyl]-7,7-dimethyl-4-bicyclo[3.1.1]hept-3-enyl] methanol (HU-308); (6aR,10aR)-3-(1,1-Dimethylbutyl)-6a,7,10,10a-tetrahydro-6,6,9-trimethyl-6H-dibenzo[b,d]pyran (JWH-133); (6aR,10aR)-1-methoxy-6,6,9-trimethyl-3-(2-methyloctan-2-yl)-6a,7,10,10a-tetrahydrobenzo[c]chromene (L-759,633); PRS 211,375 (cannabinor); aminoalkylindole such as (3-iodo-5-nitrophenyl)-[1-[(1-methylpiperidin-2-yl)methyl]indol-3-yl]methanone (AM-1241), bicyclic resorcinols and their derivatives such as 2-(3-methylcyclohexyl)-5-(1,1'-dimethylheptyl)-resorcinol isomers (O-1797 and O-1798), 2-(3R-methylcyclohexyl)-5-(1,1'-dimethylheptyl)-resorcinol (O-1826); bicyclic hydroxyl resorcinol derivatives such as 1-{4-(1,1-Dimeyhyl-heptyl)-2,6-dimethoxy-phenyl}-3-methyl-cyclohexanol (O-2137 and its racemates O-1966, and O-1967); and 3,5 dihydroxyphenyl analogues of resorcinols such as O-3853; naphthoylindole cannabinoids such as 2-Methyl-1-propyl-1H-indol-3-yl)-1-naphthalenylmethanone (JWH-015); (6aR,10aR)-1-methoxy-6,6-dimethyl-9-methylidene-3-(2-methyloctan-2-yl)-7,8,10,10a-tetrahydro-6aH-benzo[c]chromene (L-759,656); benzofuran derivatives; 2-(2,4-dichloroanilino)-N-(tetrahydropyran-4-ylmethyl)-4-(trifluoromethyl)pyrimidine-5-carboxamide (GW-842,166X); N-(Piperidin-1-yl)-1-(2,4-dichlorophenyl)-1,4-dihydro-6-methylindeno[1,2-c]pyrazole-3-carboxamide (GP-1a).

More preferred selective $CB_2$ receptor agonists are resorcinols, such as O-1966, 3,5 dihydroxyphenyl analogues of resorcinols, such as O-3853, naphthoylindole cannabinoids, such as JWH-015, and other agonists, such as JWH-133 and GP-1a. Resorcinols can include or exclude O-1966, 3,5 dihydroxyphenyl analogues of resorcinols, such as O-3853, naphthoylindole cannabinoids, such as JWH-015, and other agonists, such as JWH-133 and GP-1a. Thus, the compositions of the invention can include the selective $CB_2$ receptor agonists, O-1966 or JWH-15 or a combination of O-1966 and JWH-15.

Exemplary compounds useful for the pharmaceutical compositions described herein include compounds conforming to Formula I or pharmaceutically acceptable salts or prodrugs thereof.

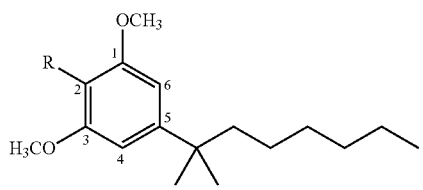

Formula I

In some embodiments, R is a cycloalkyl or thiocycloalkyl optionally substituted with C1-3 alkyl or hydroxyalkyl. An exemplary compound, O-1966 is shown below.

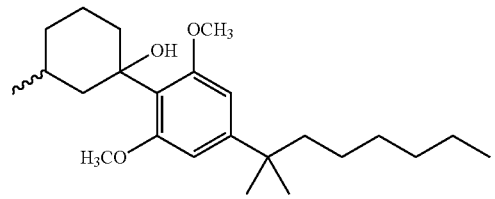

O-1966

An exemplary naphthoylindole cannabinoid, JWH-015, is shown below:

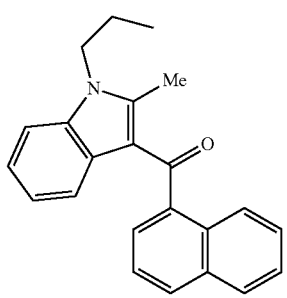

JWH-015

(2-Methyl-1-propyl-1H-indol-3-yl)-1-naphthalenylmethanone

$CB_1/CB_2$ Receptor Agonist

The "cannabinoid receptor agonist" of the current invention can be a non-selective cannabinoid receptor agonist, which binds to both cannabinoid 1 receptors ($CB_1$) and $CB_2$ receptors. A non-selective cannabinoid receptor agonist is defined as having a binding affinity ratio at $CB_1/CB_2$ receptors of less than 5. Many $CB_1/CB_2$ receptor agonists are commercially available. To enhance the immunosuppressive effect of $CB_2$ receptor activation and minimize unwanted effects, such as, but not limited to psychotropic effects associated with $CB_1$ receptor activation, the method includes administering one or more $CB_1/CB_2$ receptor agonists that exhibit activity at both $CB_1$ and $CB_2$ receptors either alone or in combination with a $CB_1$ receptor antagonist.

$CB_1/CB_2$ receptor agonists useful in the current invention are $\Delta^9$-tetrahydrocannabinol (THC, dronabinol, Marinol®); (6aR,10aR)-9-(Hydroxymethyl)-6,6-dimethyl-3-(2-methyloctan-2-yl)-6a,7,10,10a-tetrahydrobenzo [c]chromen-1-ol (HU-210); (6aR,10aR)-1-methoxy-6,6-dimethyl-9-methylidene-3-(2-methyloctan-2-yl)-7,8,10,10a-tetrahydro-6aH-benzo[c]chromene (L-759,656); aminoalkylindole cannabinoids such as (R)-(+)-[2,3-dihydro-5-methyl-3-(4-morpholinylmethyl)pyrrolo [1,2,3-de]-1,4-benzoxazin-6-yl]-1-napthalenylmethanone (WIN 55,212-2); 2-[(1R,2R,5R)-5-hydroxy-2-(3-hydroxypropyl) cyclohexyl]-5-(2-methyloctan-2-yl)phenol (CP 55,940); naphthalen-1-yl-(4-pentyloxynaphthalen-1-yl)methanone (CRA-13, SAB-378); naphthalen-1-yl-(1-pentylindol-3-yl)methanone (JWH-018, AM-678); [(6S,6aR,9R,10aR)-9-hydroxy-6-methyl-3-[(2R)-5-phenylpentan-2-yl]oxy-5,6,6a,7,8,9,10,10a-octahydrophenanthridin-1-yl] acetate (CP 50,556-1, levonantradol); (6aR,10aR)-rel-1-hydroxy-6,6-dimethyl-3-(2-methyloctan-2-yl)-7,8,10,10a-tetrahydro-6H-benzo[c] chromen-9(6aH)-one (nabilone, Cesamet®); benzofuran derivatives; cannabidiol+THC (Sativex®). $CB_1/CB_2$ receptor agonists can include or exclude $\Delta^9$-tetrahydrocannabinol (THC, dronabinol, Marinol®); (6aR,10aR)-9-(Hydroxymethyl)-6,6-dimethyl-3-(2-methyloctan-2-yl)-6a,7,10,10a-tetrahydrobenzo [c]chromen-1-ol (HU-210); (6aR,10aR)-1-methoxy-6,6-dimethyl-9-methylidene-3-(2-methyloctan-2-yl)-7,8,10,10a-tetrahydro-6aH-benzo[c]chromene (L-759, 656); aminoalkylindole cannabinoids such as (R)-(+)-[2,3-dihydro-5-methyl-3-(4-morpholinylmethyl)pyrrolo [1,2,3-de]-1,4-benzoxazin-6-yl]-1-napthalenylmethanone (WIN 55,212-2); 2-[(1R,2R,5R)-5-hydroxy-2-(3-hydroxypropyl) cyclohexyl]-5-(2-methyloctan-2-yl)phenol (CP 55,940); naphthalen-1-yl-(4-pentyloxynaphthalen-1-yl)methanone (CRA-13, SAB-378); naphthalen-1-yl-(1-pentylindol-3-yl) methanone (JWH-018, AM-678); [(6S,6aR,9R,10aR)-9-hydroxy-6-methyl-3-[(2R)-5-phenylpentan-2-yl]oxy-5,6,6a,7,8,9,10,10a-octahydrophenanthridin-1-yl] acetate (CP 50,556-1, levonantradol); (6aR,10aR)-rel-1-hydroxy-6,6-dimethyl-3-(2-methyloctan-2-yl)-7,8,10,10a-tetrahydro-6H-benzo[c]chromen-9(6aH)-one (nabilone, Cesamet®); benzofuran derivatives; cannabidiol+THC (Sativex®).

$CB_1$ Receptor Antagonist

The "cannabinoid receptor antagonist" of the current invention can be a cannabinoid receptor 1 ($CB_1$) receptor antagonist. $CB_1$ receptor antagonists bind to the $CB_1$ receptor and block the activation of $CB_1$ receptors. Antagonism of the $CB_1$ receptor may occur on the same system (e.g. immune system) that contains $CB_2$ receptors or on a different system that contains little or no $CB_2$ receptors.

$CB_1$ receptor antagonists useful in the current invention are 1,5-diarylpyrazole analogues such as rimonabant (SR141716, Acomplia®, Bethin®, Monaslim®, Remonabent®, Riobant®, Slimona®, Rimoslim®, Zimulti® and Riomont®), surinabant (SR147778) and AM251; 3,4-diarylpyrazolines such as SLV-319 (ibipinabant); 4,5-diarylimidazoles; 1,5-diarylpyrrole-3-carboxamides, bicyclic derivatives of diaryl-pyrazole and imidazoles such as CP-945,598 (otenabant); methylsulfonamide azetidine derivatives; TM38837; beta-lactam cannabinoid modulators; benzofuran derivatives. $CB_1$ receptor antagonists can include or exclude 1,5-diarylpyrazole analogues such as rimonabant (SR141716, Acomplia®, Bethin®, Monaslim®, Remonabent®, Riobant®, Slimona®, Rimoslim®, Zimulti® and Riomont®), surinabant (SR147778) and AM251; 3,4-diarylpyrazolines such as SLV-319 (ibipinabant); 4,5-diarylimidazoles; 1,5-diarylpyrrole-3-carboxamides, bicyclic derivatives of diaryl-pyrazole and imidazoles such as CP-945,598 (otenabant); methylsulfonamide azetidine derivatives; TM38837; beta-lactam cannabinoid modulators; benzofuran derivatives.

Immunosuppressive Agents

The compositions of the invention can also include or exclude one or more immunosuppressive agents. Immunosuppressive agents useful in the present invention include but are not limited to glucocorticoids; cytostatics including alkylating agents such as nitrogen mustards such as cyclophosphamide (ENDOXAN®, CYTOXAN®, NEOSAR®, PROCYTOX®, and REVIMMUNE®), nitrosoureas, such as carmustine (BiCNu®), lomustine (CeeNU®), semustine, ethylnitrosourea, streptozaotocin (ZANOSAR®), platinum compounds such as cisplatin (PLATINOL®, PLATINOL-AQ®), carboplatin (PARAPLATIN®, PARAPLATIN-AQ®), oxaliplatin (ELOXATIN®, OXALIPLATIN MEDAC®), antimetabolites including folic acid analogues such as methotrexate, purine analogues such as azathioprine (AZASAN®, IMURAN®, AZAMUN®, IMUREL®) and mercaptopurine (PURINETHOL®), pyrimidine analogues, protein synthesis inhibitors, cytotoxic antibiotics such as actinomycin D (DACTINOMYCIN®), anthracyclines, such as daunorubicin (DAUOMYCIN®), doxorubicin (ADRIAMYCIN®), mitomycin C, bleomycin (BLENOXANE®), mithramycin (MITHRACIN®); a polyclonal antibodies such as ATGAM® and THYMOGLOBULINE®; monoclonal antibodies including muromonab-CD3⁺ (Orthoclone OKT3®), basiliximab (SIMULECT®) and daclizumab (ZENAPAX®); calcineurin inhibitors such as tacrolimus (PROGRAF®, PROTOPIC®), cyclosporine (SANDIMMUNE®, NEORAL®, CICLORAL®, GENGRAF®, DEXIMUNE®, RESTASIS®); sirolimus (RAPAMUNE®); interferons such as IFN-β; opioids; TNF-α binding proteins such as infliximab (REMICADE®), etanercept (ENBREL®) or adalimumab (HUMIRA®); mycophenolic acid (CELLCEPT®, MYFORTIC®) Mycophenolate; fingolimod (GILENYA®), myriocrin, Mofetil, Prednisone.

Definitions

The terms "preventing," "blocking," "antagonizing," or "reversing" mean preventing in whole or in part, or ameliorating or controlling.

A "therapeutically effective amount" or an "effective amount" refers to the amount of an active compound, composition or dosage form comprising an active compound which is effective for producing the desired therapeutic.

A "pharmaceutical composition" is defined to mean a therapeutically effective amount of one or more active pharmaceutical ingredients along with one or more pharmaceutically acceptable excipients, diluents or carriers.

An "agonist" generally refers to an exogenous compound that binds to a receptor and mimics the effects of an endogenous compound. Further, the term "agonist" refers to both full and/or partial agonists. A full agonist shows full efficacy at a receptor, while a partial agonist shows only partial efficacy at a receptor relative to a full agonist. Selective $CB_2$ receptor agonists bind with a high affinity to the $CB_2$ receptor with either no or very low affinity to the $CB_1$ receptor thereby decreasing cAMP activity in $CB_2$ receptor expressing cells. Non-selective $CB_2$ receptors agonists (referred to as $CB_1/CB_2$ receptor agonists) may be considered either full agonists or partial agonists at both $CB_1$ and $CB_2$ receptors or some combination of a full agonist at one cannabinoid receptor (e.g. $CB_2$) and a partial agonist at the other cannabinoid receptor (e.g. $CB_1$). An inverse agonist generally refers to an exogenous compound that specifically binds to the same receptor as does an agonist, but induces opposing pharmacological effects. That is, an agonist can increase the activity of the receptor above the basal level, while an inverse agonist can decrease the activity of the receptor below the basal level.

An "antagonist" generally refers to any agent that binds to a receptor and inhibits the action of an agonist (endogenous or exogenous). Further, an antagonist is a compound that is generally devoid of any intrinsic activity and produces a response by interfering with the binding of an agonist and thereby inhibiting the action of an agonist. An antagonist can also antagonize another compound acting at the same receptor if it has higher affinity but a lower efficacy or intrinsic activity. For the instant invention, selective $CB_1$ or $CB_2$ receptor antagonists bind with a high affinity to either the $CB_1$ or the $CB_2$ receptor, respectively, with either no or very low affinity for the other cannabinoid receptor.

"Cells of the immune system" or "immune cells", is meant to include any cells of the immune system that may be assayed, including, but not limited to, B lymphocytes, also called B cells, T lymphocytes, also called T cells, natural killer (NK) cells, natural killer T (NK) cells, lymphokine-activated killer (LAK) cells, monocytes, macrophages, neutrophils, granulocytes, mast cells, platelets, Langerhan's cells, stem cells, dendritic cells, peripheral blood mononuclear cells, tumor-infiltrating (TIL) cells, gene modified immune cells including hybridomas, drug modified immune cells, antigen presenting cells and derivatives, precursors or progenitors of the above cell types.

"Immune effector cells" refers to cells, and subsets thereof, e.g. Treg, Th1, Th2, capable of binding an antigen or responding to an antigen presented by an antigen presenting cell, and which mediate an immune response selective for the antigen. These cells include, but are not limited to, T cells (T lymphocytes) and their subsets e.g. Treg, Th1, Th2, Th17; B cells (B lymphocytes), antigen presenting cells, such as for example dendritic cells, monocytes, macrophages; myeloid suppressor cells, natural killer (NK) cells and cytotoxic T lymphocytes (CTLs), for example CTL lines, CTL clones, and CTLs from tumor, inflammatory, or other infiltrates.

A "T regulatory cell" or "Treg cell" or "Tr cell" refers to a cell that can inhibit a T cell response. Treg cells express the transcription factor Foxp3, which is not upregulated upon T cell activation and discriminates Tregs from activated effector cells. Tregs are identified by the cell surface markers CD25, CD45RB, CTLA4, and GITR. Treg development is induced by mesenchymal stem cell activity and by other inductive methods including, but not limited to, activation of T-cells in the presence of IL-10 and/or TGF-β. Several Treg subsets have been identified that have the ability to inhibit autoimmune and chronic inflammatory responses and to maintain immune tolerance in tumor-bearing hosts. These subsets include interleukin 10-(IL-10-) secreting T regulatory type 1 (Tr1) cells, transforming growth factor-β-(TGF-β-) secreting T helper type 3 (Th3) cells, and "natural" $CD4^+/CD25^+$ Tregs (Trn) (Fehervari and Sakaguchi. J. Clin. Invest. 2004, 114:1209-1217; Chen et al. Science. 1994, 265: 1237-1240; Groux et al. Nature. 1997, 389: 737-742).

The immune system in mammals includes two prongs: the innate immune system and the adaptive immune system. The innate immune system, also known as the non-specific immune system defend the host from infection by other organisms in a non-specific manner. The adaptive immune system is specific for the inducing antigen, confers the ability to recognize and remember specific pathogens (to generate immunity), and to mount stronger attacks each time the pathogen is encountered.

An "innate immune response" generally refers to an immune response that is not affected by prior contact with the antigen. The main protective mechanisms of innate immunity are the skin (protects against attachment of potential environmental invaders), mucous (traps bacteria and other foreign material), gastric acid (destroys swallowed invaders), antimicrobial substances such as interferon (IFN) (inhibits viral replication) and complement proteins (promotes bacterial destruction), fever (intensifies action of interferons, inhibits microbial growth, and enhances tissue repair), natural killer (NK) cells (destroy microbes and certain tumor cells, and attack certain virus infected cells), and the inflammatory response (mobilizes leukocytes such as macrophages and dendritic cells to phagocytose invaders).

An "adaptive immune response" may be humoral (antibody based) or cellular. A adaptive immune response is established during the life of an animal, is specific for an inducing antigen, and is marked by an enhanced immune response on repeated encounters with the antigen. A key feature of the T lymphocytes of the adaptive immune system is their ability to detect minute concentrations of pathogen-derived peptides presented by MHC molecules on the cell surface. Upon activation, naive CD4 T cells differentiate into one of several cell types, including Th1, Th2 and Th17 cells, each type being characterized by the cytokines it produces. "Th1 cells" are primarily involved in activating macrophages with respect to cellular immunity and the inflammatory response, whereas "Th2 cells" or "helper T cells" are primarily involved in stimulating B cells to produce antibodies (humoral immunity). CD4 is the receptor for the human immunodeficiency virus (HIV). Effector molecules for Th1 cells include, but are not limited to, IFN-γ, GM-CSF, TNF-α, CD40 ligand, Fas ligand, IL-3, TNF-β, and IL-2. Effector molecules for Th2 cells include, but are not limited to, IL-4, IL-5, CD40 ligand, IL-3, GS-CSF, IL-10, TGF-β, and eotaxin. Activation of the Th1 type cytokine response can suppress the Th2 type cytokine response, and reciprocally, activation of the Th2 type cytokine response can suppress the Th1 type response.

The phrase "T cell response" means an immunological response involving T cells. The T cells that are "activated" divide to produce additional Th1 or Th2 cells, memory T cells or cytotoxic T cells. The cytotoxic T cells bind to and destroy cells recognized as containing the antigen. The memory T cells are activated by the antigen and thus provide a response to an antigen already encountered. This overall response to the antigen is the T cell response.

The term "transplant" includes any cell, organ, organ system or tissue which can elicit an immune response in a recipient subject mammal. In general, therefore, a transplant includes an allograft or a xenograft cell, organ, organ system or tissue. An allograft refers to a graft (cell, organ, organ system or tissue) obtained from a member of the same species as the recipient. A xenograft refers to a graft (cell, organ, organ system or tissue) obtained from a member of a different species as the recipient. The term "immune rejection," as used herein, is intended to refer to immune responses involved in transplant rejection, as well as to the concomitant physiological result of such immune responses, such as for example, interstitial fibrosis, chronic graft artheriosclerosis, or vasculitis. The term "immune rejection," as used herein, is also intended to refer to immune responses involved in autoimmune disorders, and the concomitant physiological result of such immune responses, including T cell-dependent infiltration and direct tissue injury; T cell-dependent recruitment and activation of macrophages and other effector cells; and T cell-dependent B cell responses leading to autoantibody production.

Without wishing to be bound by any theory, the compounds of the invention may exert their effects though a variety of mechanisms of action. Thus the selective $CB_2$ receptor agonist, the $CB_1/CB_2$ receptor agonist and the $CB_1$ receptor antagonist may variously suppress T cells, shift the Th1/Th2 cytokine profile to a Th2 profile, down-regulate epithelial cells and tighten the barrier formed by epithelial cells, limit influx of immune cells to a site of inflammation, inhibit cell accumulation and egress from the blood stream out into the tissue spaces, down-regulate pro-inflammatory cytokines and chemokines, which in turn can down-regulate influx of inflammatory cells (neutrophils, monoctyes/macrophages); and down-regulate epithelial cells to prevent them from expressing adhesion molecules that will allow egress of cells out of the blood vessels.

Activation of $CB_2$ and $CB_1$ receptors can be assayed using any standard method known in the art. In vitro assays using specific agonists or antagonists that have been detectably labeled can be used to determine binding activity. Alternatively, cell-based methods that assay activation of G-protein coupled receptors can be used. Like other G-protein coupled receptors, activation of cannabinoid receptors results in activation of various signal transduction pathways via different "second messengers" (e.g., calcium and/or potassium fluxes across membranes, cyclic nucleotides, and phosphoinositides). Thus, modulation in the level or activity of one or more second messengers in $CB_2$ agonist-treated cells relative to the corresponding levels in control (e.g., untreated) cells can be indicative of activation of the G-protein coupled receptor complex. Assessing second messenger activity is routine in the art, and kits and reagents for performing such assays are readily available from commercial sources. For example, alterations in calcium levels can be assayed with calcium-sensitive dyes such as Calcium Crimson-AM (Invitrogen, Calrsbad, Calif.), FLIPR (Molecular Devices, Sunnyvale, Calif.), Fluo4 and Fura Red (Caliper Life Sciences, Hopkinton, Mass.), which can be monitored either by microscopy or fluorometry. Modulation of cyclic nucleotides can be assayed by chemiluminescence, immunoassays, or fluorescence polarization techniques. Changes in phosphoinisitide levels can be evaluated by fluorescence polarization, immunoassays and other downstream markers such as D-myo-inositol 1-phosphate.

Receptor activation can also be monitored in cell-based assays that measure the impact of $CB_2$ agonists, $CB_1/CB_2$ agonists and $CB_1$ antagonists on specific cell functions and/or on cell survival generally. Methods of measuring various cell functions and survival are well-known in the art. In the context of the present invention, suitable assays include, without limitation, cell migration assays, apoptosis assays, the mixed lymphocyte reaction, in vitro antibody formation in the plaque-forming cell assay, responses to mitogens, and natural killer cell activity. Alternatively or in addition, receptor activation can be monitored by assaying levels of downstream markers, for example, levels of cytokines or chemokines or other immune related markers, e.g., IL-10 and CD40L. Alternatively, or in addition, other markers or relating to cell status, e.g., Socs5, Sla2, and Cyclin D3 can also be assayed. Such assays are routine in the art and can include immuno-assays, e.g., ELISA methods or nucleic acid based methods, e.g., RT-PCR or gene array analysis.

Dosage/Formulation/Administration

Pharmaceutical compositions for use in accordance with the present invention may be formulated in a conventional manner using one or more physiologically acceptable carriers or excipients. As noted above, the compositions can include a selective $CB_2$ receptor agonist or $CB_1/CB_2$ receptor agonist alone or in combination with a $CB_1$ receptor antagonist and/or an immunosuppressive agent. Thus, the compositions can include one or more selective $CB_2$ receptor agonists, or one or more $CB_1/CB_2$ receptor agonists, or a combination of one or more selective $CB_2$ receptor agonists and a combination of one or more $CB_1/CB_2$ receptor agonists. For example, the compositions can include O-1966 or JWH-15 or a combination of O-1966 and JWH-15. In some embodiments, the compositions can include one or more $CB_1$ receptor antagonists and or one or more immunosuppressive agents. The particular combination of agonists/antagonists/immunosuppressive agents can vary according to many factors, for example, the particular kind of graft, the immunocompatibility between the recipient and the donor, and the health of the recipient. Regardless of the specific combination, the compositions can be administered directly to a mammal. Generally, the compositions can be suspended in a pharmaceutically acceptable carrier (e.g., physiological saline or a buffered saline solution) to facilitate their delivery. Encapsulation of the compositions in a suitable delivery vehicle (e.g., polymeric microparticles or implantable devices) may increase the efficiency of delivery. A composition can be made by combining any of the compositions provided herein with a pharmaceutically acceptable carrier. Where the selective $CB_2$ receptor agonists or $CB_1/CB_2$ receptor agonists, the $CB_1$ receptor antagonists or the immunosuppressive agents are administered to the same patient, they can be administered in a single formulation or in separate formulations (which may be the same or different) that are administered concurrently or sequentially.

The compositions can be formulated in various ways for parenteral or non-parenteral administration. Where suitable, oral formulations can take the form of tablets, pills, capsules, or powders, which may be enterically coated or otherwise protected. Sustained release formulations, suspensions, elixirs, aerosols, and the like can also be used.

Pharmaceutically acceptable carriers and excipients can be incorporated (e.g., water, saline, aqueous dextrose, and glycols, oils (including those of petroleum, animal, vegetable or synthetic origin), starch, cellulose, talc, glucose, lactose, sucrose, gelatin, malt, rice, flour, chalk, silica gel, magnesium stearate, sodium stearate, glycerol monosterate, sodium chloride, dried skim milk, glycerol, propylene glycol, ethanol, and the like). The compositions may be subjected to conventional pharmaceutical expedients such as sterilization and may contain conventional pharmaceutical additives such as preservatives, stabilizing agents, wetting or emulsifying agents, salts for adjusting osmotic pressure, buffers, and the like. Suitable pharmaceutical carriers and their formulations are described in "Remington's Pharmaceutical Sciences" by E. W. Martin, which is herein incorporated by reference. Such compositions will, in any event, contain an effective amount of the compositions together with a suitable amount of carrier so as to prepare the proper dosage form for proper administration to the patient.

The methods of the present invention can be instigated when a patient is specifically in need of immediate relief from the symptoms of graft rejection or autoimmune disease or to preclude or lessen the risk of or severity of such symptoms. Thus, the present methods can include a step of identifying a patient in need of treatment.

Any composition described herein can be administered to any part of the host's body for subsequent delivery to a selective $CB_2$ receptor agonists or $CB_1/CB_2$ receptor agonist responsive cell. A composition can be delivered to, without limitation, the bones, bone marrow, joints, nasal mucosa, blood, lungs, intestines, muscle tissues, skin, or the peritoneal cavity of a mammal. In terms of routes of delivery, a composition can be administered by intravenous, intraperitoneal, intramuscular, subcutaneous, intramuscular, intrarectal, intravaginal, intrathecal, intratracheal, intradermal, or transdermal injection, by oral or nasal administration, or by gradual perfusion over time. In a further example, an aerosol preparation of a composition can be given to a host by inhalation.

The dosage required will depend on the route of administration, the nature of the formulation, the nature of the patient's illness, the patient's size, weight, surface area, age, and sex, other drugs being administered, and the judgment of the attending clinician. Wide variations in the needed dosage are to be expected in view of the variety of selective $CB_2$ receptor agonists or $CB_1/CB_2$ receptor agonists, $CB_1$ receptor antagonists and immunosuppressive agents available and the differing efficiencies of various routes of administration. Variations in these dosage levels can be adjusted using standard empirical routines for optimization, as is well understood in the art. Administrations can be single or multiple (e.g., 2- or 3-, 4-, 6-, 8-, 10-, 20-, 50-, 100-, 150-, or more fold). Encapsulation of the selective $CB_2$ receptor agonists or $CB_1/CB_2$ receptor agonists, $CB_1$ receptor antagonist and/or an immunosuppressive agent in a suitable delivery vehicle (e.g., polymeric microparticles or implantable devices) may increase the efficiency of delivery.

The duration of treatment with any composition provided herein can be any length of time from as short as one day to as long as the life span of the host (e.g., many years). For example, the compositions can be administered once a week (for, for example, 4 weeks to many months or years); once a month (for, for example, three to twelve months or for many years); or once a year for a period of 5 years, ten years, or longer. It is also noted that the frequency of treatment can be variable. For example, the present compositions can be administered once (or twice, three times, etc.) daily, weekly, monthly, or yearly.

The particular dosage of a pharmaceutical composition to be administered to the patient will depend on a variety of considerations including the nature of the disease or condition (e.g., the extent of compatibility of a transplant or the severity of an autoimmune disease), the schedule of administration, the age and physical characteristics of the patient, and other considerations known to those of ordinary skill in the art. Dosages can be established using clinical approaches known in the art. It is presently believed that dosages of selective CB2 receptor agonists, $CB_1/CB_2$ receptor agonists, or $CB_1$ receptor antagonists in the range of 0.1 to 100 mg of agonist per kilogram of the patient's body weight will be useful, and a range of 1 to 100 mg per kg is generally preferred, particularly where administration is by injection or ingestion. Exemplary dosages include 0.1 mg/kg, 0.5 mg/kg, 1.0 mg/kg, 2.0 mg/kg, 3.0 mg/kg, 4.0 mg/kg, 5.0 mg/kg, 6.0 mg/kg, 7.0 mg/kg, 8.0 mg/kg, 9.0 mg/kg, 10.0 mg/kg, 12.0 mg/kg, 15.0 mg/kg, 18.0 mg/kg, 20.0 mg/kg, 25.0 mg/kg, 30.0 mg/kg, 35.0 mg/kg, 40.0 mg/kg, 45.0 mg/kg, 50.0 mg/kg, 55.0 mg/kg, 60.0 mg/kg, 65.0 mg/kg, 70.0 mg/kg, 75.0 mg/kg, 80.0 mg/kg, 85.0 mg/kg, 90.0 mg/kg, 95.0 mg/kg, 100.0 mg/kg, 150.0 mg/kg, 200.0 mg/kg, 250.0 mg/kg, 300.0 mg/kg, 350.0 mg/kg, 400.0 mg/kg, 500.0 mg/kg, and 1000.0 mg/kg. Topical dosages may utilize formulations containing generally as low as 0.1 mg of selective $CB_2$ receptor agonist or $CB_1/CB_2$ receptor agonist per ml of liquid carrier or excipient, with multiple applications being made as necessary. In some embodiments, the dosages can be in the range of 0.01-1,000 µg/kg.

The dosages of immunosuppressants can vary according to the specific immunosuppressive agent, the health and physical condition of the recipient, and the nature of the transplanted tissue. It is to be expected that the administration of one or more selective $CB_2$ receptor agonists, $CB_1/CB_2$ receptor agonists, or $CB_1$ receptor antagonists may allow the use of lower dosages of immunosuppressants, thus reducing side effects, that would otherwise be needed in the absence of selective $CB_2$ receptor agonists, $CB_1/CB_2$ receptor agonists, or $CB_1$ receptor antagonists.

The agonists described herein can be administered in "therapeutically effective amounts," in which case they are administered in amounts that are or are expected to be effective, either upon a single- or multiple dose administration to a patient, in preventing, curing, reducing the severity of, or ameliorating one or more symptoms of a condition or disorder described herein (e.g., graft-versus-host disease or an autoimmune disease). A therapeutically effective amount is an amount that brings about or is expected to bring about a clinically beneficial outcome (e.g., the prolonged survival of a graft).

While the present methods clearly contemplate the treatment and prevention of graft rejection and autoimmune disease in human patients, the invention is not so limited. Veterinary uses are also within the scope of the present invention. Accordingly, the present methods can be applied to treat mammalian, e.g., humans, non-human primates, domestic animals e.g., dogs, cats, pigs, horses, cows, sheep and goats; and avian subjects, e.g., chickens.

As noted above, the present compositions and methods can be used in any instance in which a host receives a graft of biological material other than an autograft. The graft can be the transplant of a heart, kidney, liver, lung, pancreas, bone marrow, cartilage, skin, cornea, neuronal tissue, muscle, or of tissues, portions or cells of these organs (e.g., a lobe of a lung or liver). The graft recipient can be treated with a selective $CB_2$ receptor agonist or $CB_1/CB_2$ receptor agonist. The treatment can also include administration of a $CB_1$ receptor antagonist and/or an immunosuppressive agent. In some embodiments, the donor or donor tissue can be treated with a selective $CB_2$ receptor agonist or $CB_1/CB_2$ receptor agonist.

Autoimmune diseases can be treated as described herein with an a selective $CB_2$ receptor agonist or $CB_1/CB_2$ receptor agonist, and optionally with a $CB_1$ receptor antagonist and/or an immunosuppressive agent. Autoimmune diseases amenable to treatment include diabetes mellitus (e.g., type I diabetes); multiple sclerosis; an arthritic disorder (e.g., rheumatoid arthritis (RA), juvenile rheumatoid arthritis, osteoarthritis, psoriatic arthritis, or ankylosing spondylitis (preferably, RA)); myasthenia gravis; vasculitis; systemic lupus erythematosus (SLE); glomerulonephritis; autoimmune thyroiditis; a skin inflammatory disorder (e.g., dermatitis (including atopic dermatitis and eczematous dermatitis), scleroderma, or psoriasis); lupus erythematosus; a fibrosis or fibrotic disorder (e.g., pulmonary fibrosis or liver fibrosis); a respiratory disorder (e.g., asthma or COPD); an atopic disorder (e.g., including allergy); or an intestinal inflammatory disorder (e.g., an IBD such as Crohn's disease or ulcerative colitis).

Any method known to one of ordinary skill in the art can be used to determine if a particular response is induced. Clinical methods that can assess the degree of a particular disease state can be used to determine if a response is induced. For example, in a transplant patient, clinical methods can include blood tests to assess organ function, ultrasound analysis of the size of the transplanted organ and blood flow, x-rays, biopsies, electrocardiograms and echocardiograms to monitor heart function, pulmonary function tests, molecular analysis such as AlloMap™ to monitor the activity of specific genes in white blood cells to determine the risk of acute cellular rejection. The particular methods used to evaluate a response will depend upon the nature of the patient's disorder, the patient's age, and sex, other drugs being administered, and the judgment of the attending clinician.

In some embodiments, the methods to determine if a particular response is induced can include comparing a patient's sample with standard reference levels for the particular marker or assay. Standard reference levels typically represent the levels derived from a large population of individuals. The reference population may include individuals of similar age, body size; ethnic background or general health as the individual in question. Thus for example, marker levels in a patient's sample can be compared to values derived from: 1) individuals who have not received a graft; 2) individuals who have successfully received a graft, i.e., individuals in which the graft has not been rejected; and/or 3) individuals who have rejected a graft. Any population size can be used to determine the reference levels. For example, a population of between 2 and 250, e.g., 2, 3, 4, 5, 10, 15, 20, 25, 30, 40, 50, 100, 150, 200, 250 or more individuals can be used to determine the average reference levels, with greater accuracy in the measurement coming from larger sample populations.

The compositions provided herein can be administered in conjunction with other therapeutic modalities to an individual in need of therapy. The present compounds can be given prior to, simultaneously with or after treatment with other agents or regimes. For example, the selective $CB_2$ receptor or $CB_1/CB_2$ receptor agonists, and optionally with a $CB_1$ receptor antagonist and/or an immunosuppressive agent can be administered in conjunction with standard therapies used in organ transplantation. In addition to immunosuppressant drugs, other medications may include: antibiotics, anti-fungal medications, anti-ulcer medications, diuretics, antivirals or statins.

Any suitable concentration of an active pharmaceutical ingredient may be used, where the active pharmaceutical ingredient is administered in an effective amount to achieve its intended purpose. Determination of a therapeutically effective amount for a particular active ingredient is well within the capability of persons skilled in the art.

The specific therapeutically effective dose level for any particular patient will depend upon a variety of factors including the type and location of the tissue being transplanted; activity of the specific compound employed; the specific composition employed; the age, body weight, general health, sex and diet of the patient; the time of administration, route of administration, and rate of excretion of the specific compound employed; the duration of the treatment; drugs used in combination or coincidentally with the specific compound employed; and like factors well known in the medical arts.

The therapeutically effective dose of the pharmacologic agent can be administered using any medically acceptable mode of administration. Although the skilled artisan would contemplate any of the modes of administration known to one of ordinary skill, preferably the pharmacologic agent is administered according to the recommended mode of administration, for example, the mode of administration listed on the package insert of a commercially available agent. In some embodiments, the dose may comprise 0.01 mg to about 1 g/kg/day.

The compounds described herein may be administered directly, they may also be formulated to include at least one pharmaceutical acceptable carriers, diluents, excipients, adjuvants, fillers, buffers, preservatives, lubricants, solubilizers, surfactants, wetting agents, masking agents, coloring agents, flavoring agents, and sweetening agents. Also, as described herein, such formulation may also include other active agents, for example, other therapeutic or prophylactic agents.

Methods of making a pharmaceutical composition include admixing at least one active compound, as defined above, together with one or more other pharmaceutically acceptable ingredients, such as carriers, diluents, excipients, and the like. When formulated as discrete units, such as tablets or capsule, each unit contains a predetermined amount of the active compound.

An acceptable carrier refers to those carriers that cause at most, little to no irritation, provide suitable preservation if needed, and deliver one or more cannabinoid receptor agents and/or a immunosuppressive agent of the present invention in a homogenous dosage. Pharmaceutically acceptable carriers can include any and all solvents, dispersion media, coatings, antibacterial and antifungal agents, isotonic and absorption delaying agents, and the like that are physiologically compatible, sterile aqueous solutions or dispersions and sterile powders for the extemporaneous preparation of sterile injectable solutions or dispersion. The use of such media and agents for pharmaceutically active substances is well known in the art. Supplementary active compounds can also be incorporated into the compositions.

For ophthalmic, otic, or pulmonary delivery, cannabinoid receptor agents may be combined with ophthalmologically, optically, or pulmonary acceptable preservatives, co-solvents, surfactants, viscosity enhancers, penetration enhancers, buffers, sodium chloride, or water to form an aqueous, sterile suspension or solution.

The formulations may be prepared by any methods well known in the art of pharmacy. The formulation may be prepared to provide for rapid or slow release; immediate, delayed, timed, or sustained release; or a combination thereof. Formulations may be in the form of liquids, solutions, suspensions, emulsions, elixirs, syrups, electuaries, mouthwashes, drops, tablets, granules, powders, lozenges, pastilles, capsules, gels, pastes, ointments, creams, lotions, oils, foams, sprays, mists, or aerosols. Formulations may be provided as a patch, adhesive plaster, bandage, dressing, or in the form of depot or reservoir. Many methods for the preparation of such formulations are known to those skilled in the art.

In certain embodiments, preparation of a sterile ointment formulation can include the combination of the cannabinoid receptor agents with a preservative in an appropriate vehicle, such as mineral oil, liquid lanolin, or white petrolatum.

Routes of Administration

In certain embodiments, pharmaceutical compositions of the present invention may be formulated for administration by any route of administration, including but not limited to systemic, peripheral, or topical. Illustrative routes of administration include, but are not limited to, oral, such as by ingestion, buccal, sublingual, transdermal including, such as by a patch, plaster, and the like, transmucosal including, such as by a patch, plaster, and the like, intranasal, such as by nasal spray, ocular, such as by eye drops, pulmonary, such as by inhalation or insufflation therapy using, such as via an aerosol through the mouth or nose, rectal, such as by suppository or enema, vaginal, such as by pessary, parenteral, such as by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and by implant of a depot or reservoir, such as intramuscularly. Methods of preparing pharmaceutical formulations are well known in the art. Dosage of the pharmaceutical compositions may vary by route of administration. Certain administration methods may include the step of administering the composition one or more times a day to obtain the desired therapeutic effect.

Articles of Manufacture

The compounds described herein can be packaged in suitable containers labeled, for example, for use as a therapy to treat graft rejection. The containers can include one or more compounds, e.g., one or more selective $CB_2$ receptor agonists, or one or more $CB_1/CB_2$ receptor agonists, or a combination of one or more selective $CB_2$ receptor agonists and a combination of one or more $CB_1/CB_2$ receptor agonists, or one or more $CB_1$ receptor antagonists and or one or more immunosuppressive agents, and one or more of a suitable stabilizer, carrier molecule, flavoring, and/or the like, as appropriate for the intended use. Accordingly, packaged products (e.g., sterile containers containing one or more of the compounds described herein and packaged for storage, shipment, or sale at concentrated or ready-to-use concentrations) and kits, including at least one compound of the invention and instructions for use, are also within the scope of the invention. A product can include a container (e.g., a vial, jar, bottle, bag, or the like) containing one or more compounds of the invention. In addition, an article of manufacture further may include, for example, packaging materials, instructions for use, syringes, buffers or other control reagents for treating or monitoring the condition for which prophylaxis or treatment is required. The product may also include a legend (e.g., a printed label or insert or other medium describing the product's use (e.g., an audio- or videotape)). The legend can be associated with the container (e.g., affixed to the container) and can describe the manner in which the compound therein should be administered (e.g., the frequency and route of administration), indications therefor, and other uses. The compounds can be ready for administration (e.g., present in dose-appropriate units), and may include a pharmaceutically acceptable adjuvant, carrier or other diluent and/or an additional therapeutic agent. Alternatively, the compounds can be provided in a concentrated form with a diluent and instructions for dilution.

In certain further embodiments, modes of administration can include tablets, pills, and capsules, all of which are capable of formulation by one of ordinary skill in the art.

EXAMPLES

Example 1

A Selective $CB_2$ Receptor Antagonist, but not a Selective $CB_1$ Receptor Antagonist, Blocked Suppression of the Mixed Lymphocyte Reaction by JWH-015 and O-1966

To assess the immunosuppressive properties of JWH-015 and O-1966 as a possible mechanism to minimize graft rejection in transplant patients, the one-way mixed lymphocyte reaction (MLR) assay was used. The MLR assay is a common method used to evaluate the cellular immune responses from two different individuals or animals and is considered to be an in vitro correlate of skin and organ transplant rejection. Lymphocytes from two different populations can be incubated together in which the T cells recognize the foreign cells from the other strain, become activated, proliferate and take up tritiated thymidine ([$^3$H]-thymidine). Results from this assay (Examples 1, 2 and 4) are expressed as a Suppression Index (SI), where untreated spleen cells are given a value of 1.00 (100%), and responses of cultures receiving treatment with cannabinoids are calculated as:

$$SI = \frac{\text{mean counts per minute of treated cultures}}{\text{mean counts per minute of untreated cultures}}$$

All SI data were transformed to normalized ranks to accommodate non-normality of the data. ANOVA was used to test for significant differences between groups.

First, spleen cells were obtained from six week-old, specific pathogen-free C3HeB/FeJ and C57BL/6J female mice (Jackson Laboratories; Bar Harbor, Me.). Founder $CB_2$ receptor deficient ($CB_2R^{-/-}$) mice, on a C57BL/6J background (National Institutes of Health; Bethesda, Md.) were bred in the Animal Core of the Center for Substance Abuse Research P30 Center for Excellence. Next, the T cells from one strain were treated with mitomycin C to block proliferation, while the T cells from the other strain continued to respond to the foreign cells by proliferating. More specifically, responder spleen cells were obtained in single cell suspension from C57BL/6 mice. Splenocytes from C3HeB/FeJ mice were similarly prepared and inactivated by treatment with 25 µg/ml of mitomycin C to serve as the stimulator cells. Responder cells ($8 \times 10^5$) and stimulator cells ($8 \times 10^5$) were then co-cultured in 96 well plates for 48 hours at 37° C. in RPMI with 10% fetal bovine serum, 50 µM 2-mercaptoethanol, and 100 U/ml penicillin and streptomycin sulfate. Cultures were pulsed with 1 µCi/well [$^3$H]-thymidine and harvested 18 hours later. [$^3$H]-thymidine incorporation was measured by liquid scintillation. Selective cannabinoid receptor agonists were added to responder cells 3 hours prior to mixing with stimulator cells. If cannabinoid receptor antagonists were used, they were added to responder spleen cells 2 hours prior to the addition of the cannabinoid receptor agonists.

Figure 1B:
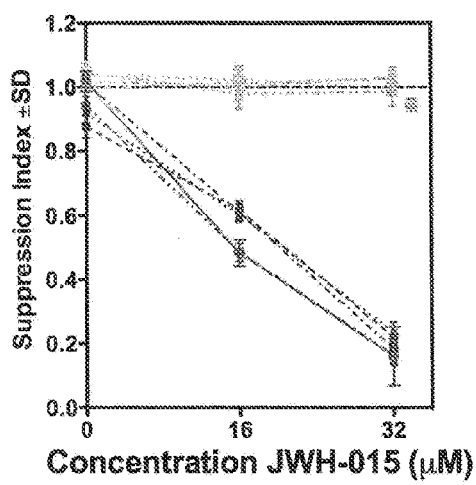

The inventors have previously shown that the nonselective cannabinoid receptor agonists, including THC inhibit the MLR when added to unfractionated murine spleen cells. The aim of the next series of experiments was to test the hypothesis that suppression of proliferation in the MLR is a $CB_2$ receptor-mediated function. For this, MLR cultures of unfractionated spleen cells from wild-type mice (WT) were exposed to selective $CB_2$ receptor agonists after pretreatment with selective $CB_1$ (SR141716A; 32 µM, 64 µM, 160 µM, 320 µM) and $CB_2$ receptor antagonists (SR144528; 32 µM, 64 µM, 160 µM, 320 µM). Responder splenocytes ($8 \times 10^5$ C57BL/6) from WT mice were treated for 3 hours with JWH-015 (16 µM and 32 µM) or ethanol vehicle (0.5%; FIG. 1A) or O-1966 (16 µM and 32 µM) or DMSO vehicle (FIG. 1B). Following this incubation, 8×10⁵ mitomycin C inactivated C3HeB/FeJ splenocytes were added to each well.

These data demonstrated that the selective $CB_2$ receptor agonists, JWH-015 and O-1966, both markedly inhibited the MLR in WT mice (FIG. 1). The data using the antagonists showed that only the $CB_2$ receptor antagonist, but not the $CB_1$ receptor antagonist, blocked the immunosuppresive effect following exposure to JWH-015 and O-1966 at both drug concentrations tested.

These results confirmed that suppression of cell proliferation by these compounds is mediated through $CB_2$, not $CB_1$, receptors.

Lastly, cultures were run in parallel with each experimental MLR and tested by flow cytometry to assess viability using LIVE/DEAD® Fixable Dead Cell Stain Kit (Molecular Probes, Inc.; Eugene, Oreg.). Cells (1×10⁶) from the culture were resuspended in 1 ml FCM Staining Buffer and incubated for 30 min at room temperature with 1 µl dead cell stain. Cells were washed twice and resuspended in FCM staining buffer and analyzed using an LSRII (BD Biosciences) flow cytometer, and the data were analyzed using FACSDiva™ software (BD Biosciences).

Figure 2:
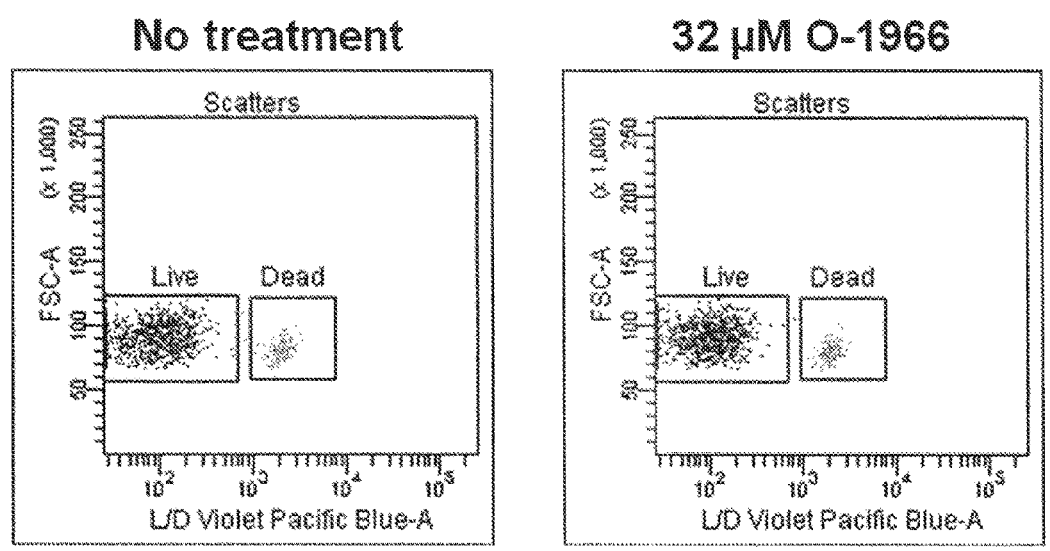
FIG. 2 is a scatter plot showing that exposure to the selective $CB_2$ receptor agonist O-1966 did not affect cell death. Using flow cytometry to assess cell viability, no change was observed in the number of live versus dead cells in untreated cultures compared to cultures exposed to O-1966.

Treatment with selective $CB_2$ receptor agonists had no effect on cell death compared to control (FIG. 2).

Example 2

JWH-015 and O-1966 Inhibited the MLR with Splenocytes from wild-type Mice, but not $CB_2R^{(-/-)}$ Knockout Mice To test the hypothesis that selective cannabinoid receptor agonists act specifically through the $CB_2$ receptor to suppress proliferation, MLR cultures of unfractionated spleen cells from WT and $CB_2$ receptor knockout (KO) mice were exposed to selective $CB_2$ receptor agonists. One advantage of utilizing receptor KO models is that the involvement of cannabinoid receptor subtypes in immune system functions can be studied. The primary outcome measure of the MLR assay (described in Example 1) of the experiments in Example 2 was also inhibition of proliferation, as the measure of immunosuppression, after exposure to selective $CB_2$ receptor agonists. For this assay, responder splenocytes (8×10⁵ C57BL/6) from WT or $CB_2R^{(-/-)}$ KO mice were treated for 3 hours with JWH-015 (8, 16 and 32 µM) or ethanol vehicle (FIG. 3A) or O-1966 (10, 30 and 50 µM) or DMSO vehicle (FIG. 3B). Following this incubation, 8×10⁵ mitomycin C inactivated C3HeB/FeJ splenocytes were added to each well. Both selective $CB_2$ receptor agonists, JWH-015 (8, 16 and 32 µM) and O-1966 (10, 30 and 50 µM) significantly (p<0.01) inhibited the MLR and reduced the SI in a dose-dependent manner (FIG. 3) in WT mice ($CB_2^{+/+}$), but not in mice lacking the $CB_2$ receptor ($CB_2^{-/-}$) at all drug concentrations tested.

These results demonstrated that suppression of cell proliferation is a mediated through activation of $CB_2$, not $CB_1$, receptors.

Example 3

JWH-015 and O-1966 Suppressed IL-2 Release in the MLR with Splenocytes from Wildtype Mice, but not $CB_2R^{(-/-)}$ Knockout Mice To corroborate whether T-cell function (as indicated from the results using the MLR assay, FIGS. 1-3) was decreased by selective $CB_2$ receptor agonists, IL-2 release was quantified by ELISA using MLR culture supernatants of unfractionated spleen cells. To carry out the ELISA immunoassay (Quantikine® Mouse IL-2 Immunoassay; R&D Systems, Inc., Minneapolis, Minn.), microplates (96 wells) were obtained pre-coated with a polyclonal antibody specific for mouse IL-2. Next, the supernatant was incubated for 2 hours at room temperature, after which any unbound antigen was removed and an enzyme-linked polyclonal antibody for mouse IL-2 was added and incubated at room temperature for 2 hours. Unbound antibody was then removed, a substrate solution added, and the optical density was determined (POLARstar Omega microplate reader; BMG LABTECH, Offenburg, Germany).

Figure 4A:
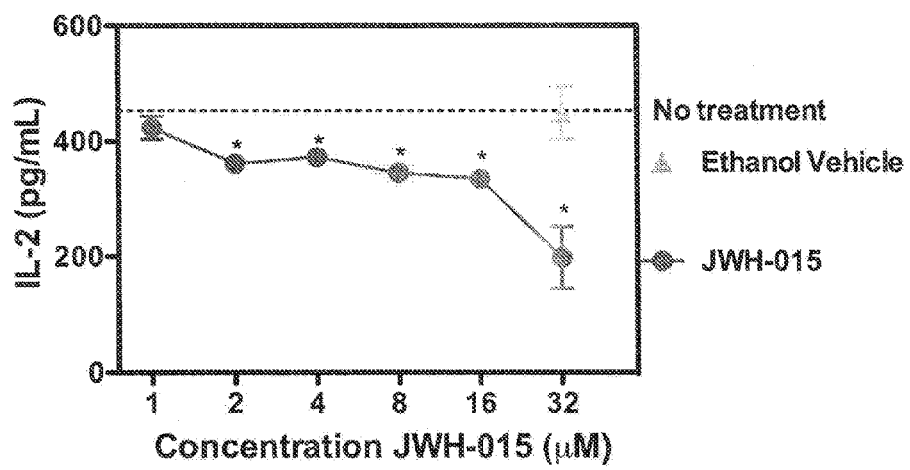
FIGS. 4A and 4B are graphs showing that both selective $CB_2$ receptor agonists, JWH-015 and O-1966, suppressed IL-2 release in the mixed lymphocyte reaction with splenocytes from wild-type (WT) mice. O-1966 did not suppress IL-2 in cells of $CB_2R^{(-/-)}$ knockout (KO) mice.
Figure 4B:
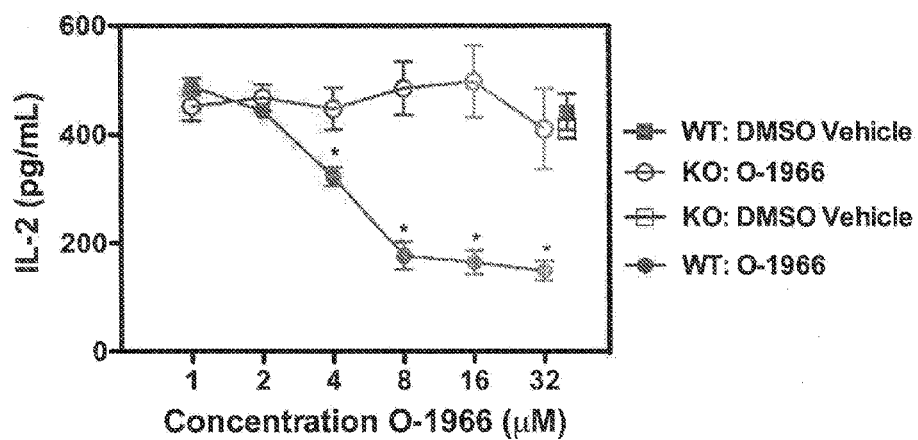

Responder splenocytes (8×10⁵ C57BL/6) from WT (FIG. 4A) or $CB_2R^{(-/-)}$ KO mice (FIG. 4B) were treated for 3 hours with JWH-015 or ethanol vehicle (FIG. 4A) or O-1966 or DMSO vehicle (FIG. 4B). Following this incubation, 8×10⁵ mitomycin C inactivated C3HeB/FeJ splenocytes were added to each well. Culture supernatants were collected at 24 hours and assayed for IL-2 release by ELISA. JWH-015 significantly (p<0.01) inhibited the release of IL-2 from WT splenocytes with the most profound inhibition at the highest concentration tested (32 µM, FIG. 4). Similarly, O-1966 significantly (p<0.01) inhibited the release of IL-2 in WT splenocytes with a profound inhibition at 8, 16 and 32 µM but was without effect on splenocytes from $CB_2R^{(-/-)}$ KO mice.

Together, these results demonstrated that both selective $CB_2$ receptor agonists inhibited IL-2 release in a dose-dependent manner, indicating that $CB_2$ receptor activation inhibits this parameter of T cell function.

Example 4

JWH-015 and O-1966 Primarily Suppressed T-Cells

To determine which cell type(s) are targeted by selective $CB_2$ receptor agonists in the MLR, mouse spleen cells (C57BL/6 splenocytes) were sorted into highly purified subpopulations using flow cytometry (FCM). For this, splenocytes were resuspended in FCM staining buffer: 1×PBS containing 1% BSA (Sigma, St. Louis, Mo.). Next, cells were incubated with 1 µg/million cells 2.4G2 antibody specific for Fcγ III/II receptor at 4° C. for 5 minutes to prevent nonspecific binding. Cells were then incubated with 0.5 µg/10⁶ cells of PE-conjugated rat anti-mouse CD11b and PerCP-conjugated rat anti-mouse CD3c for 30 min on ice followed by a washing (2×) with sorting buffer (1×PBS containing 0.1% BSA; Sigma). Cells were finally resuspended in sorting buffer to a concentration of 40×10⁶ cells/ml and sorted (FACSAria™ system; BD Biosciences, San Jose, Calif.).

Figure 5A:
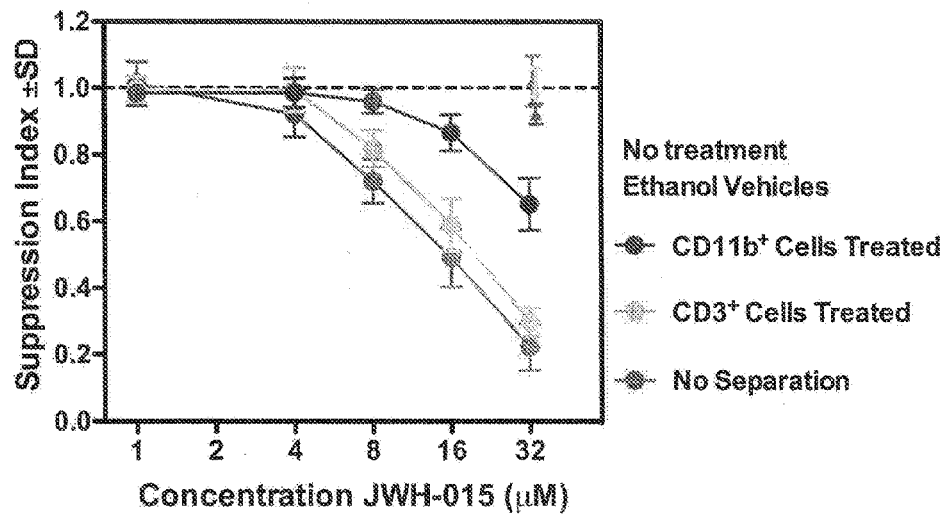
FIGS. 5A and 5B are graphs showing that both selective $CB_2$ receptor agonists, JWH-015 and O-1966, suppressed T-cells in the mixed lymphocyte reaction.
Figure 5B:
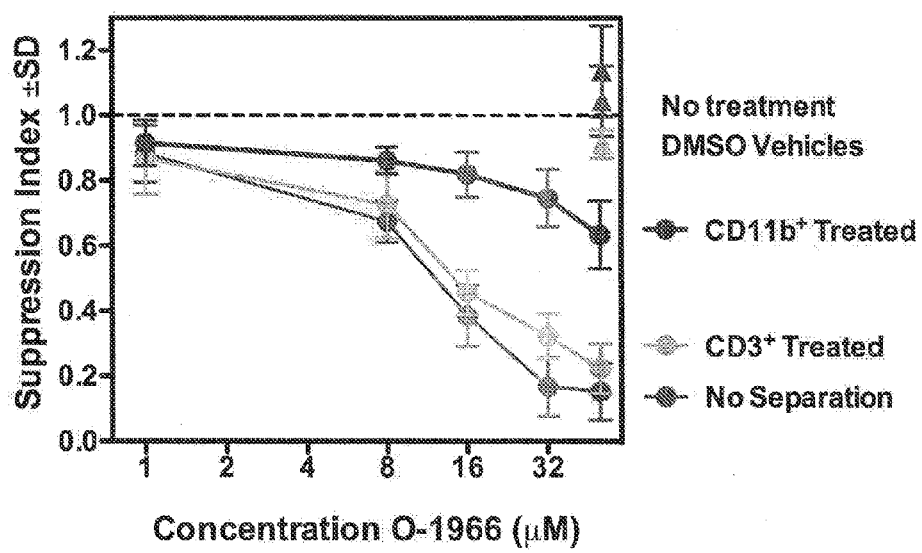

More specifically, CD11b⁺ cells (myeloid derived cells: monocytes, granulocytes, and macrophages), and CD3⁺ cells (T cells) were sorted into fractions. Next, CD11b⁺ or CD3⁺ fractions were treated with JWH-015 (1, 2, 4, 8, 16, and 32 µM) or ethanol vehicle (FIG. 5A) or O-1966 (1, 2, 4, 8, 16, and 32 µM) or DMSO vehicle (FIG. 5B) for 3 hours. Treated cells were washed 3 times before being added back to untreated populations to reconstitute normal splenocyte populations. Cells (8×10⁵) were added to each well followed by the addition of 8×10⁵ mitomycin C inactivated C3HeB/FeJ splenocytes.

Both JWH-015 and O-1966 selectively reduced the SI values for cultures in which the CD3⁺ cells were treated as compared to ones where the CD11b⁺ cells were treated indicating that $CB_2$ receptor activation induced suppression in the MLR assay (described in Example 1) is mainly through action on T cells.

These results elucidated the possible mechanisms of $CB_2$ receptor compounds in the MLR, and provide additional support for the potential of selective $CB_2$ receptor agonists as immunosuppressive agents that may be useful therapies to block graft rejection in humans.

Example 5

Figure 6:
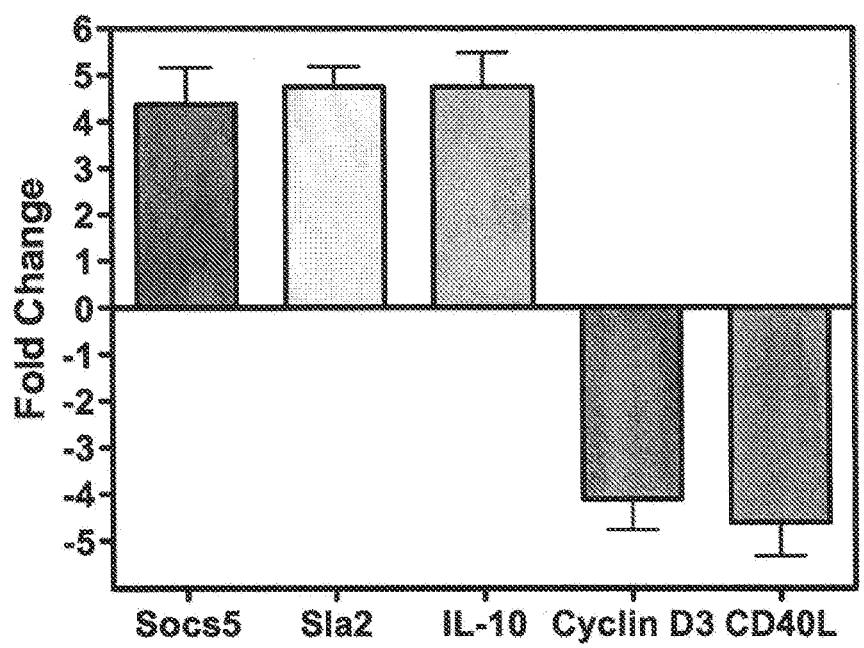
FIG. 6 is a graph showing that O-1966 modulated mRNA expression of Socs5, Sla2, IL-10, Cyclin D3 and CD40L.

The selective $CB_2$ receptor agonist, O-1966, increased mRNA expression of Socs5, Sla2, and IL-10 and decreased mRNA expression of Cyclin D3 and CD40L in T-cells in the MLR This experiment was carried out to screen for molecules that are modulated by exposure of mouse spleen cells to the $CB_2$ receptor agonist (FIG. 6). The experiment used a commercial microarray (Qiagen) that tests the levels of 89 different mRNAs. Spleen cells were placed in culture to carry out a standard Mixed Lymphocyte Reaction (MLR) assay. Experimental wells received 32 μM/ml of the selective $CB_2$ receptor agonist, O-1966, and control wells received vehicle (0.4% ethanol). Cells were harvested after 18 hours and were sorted by flow cytometry to collect the $CD3^+$ T-cell population, as these cells had previously been shown to be the ones affected by the cannabinoid. mRNA was extracted from this cell population; it was reverse transcribed; and qPCR was performed to assess which genes were altered in their expression by exposure to the cannabinoid. The results showed that O-1966 treatment increased expression of Socs5 by 4.37 fold, Sla2 by 4.75 fold, and IL-10 by 4.74 fold. O-1966 treatment decreased expression of Cyclin D3 by −4.10 fold and CD40L by −4.60 fold. These results were thought to be significant because Socs5 negatively regulates cytokine signaling, Sla2 down-regulates T-cell responses by inhibiting calcium mobilization, and IL-10 is an imunosuppressive molecule with pleiotropic effects. The decrease in CD40L and Cyclin D3 mRNA was significant because CD40L is an activation molecule for T-cells, and Cyclin D3 is a molecule involved in cell division. T-cell activation and division are decreased after exposure to the selective $CB_2$ receptor agonist.

Example 6

O-1966 increased IL-10 release in the MLR and suppression of proliferation by O-1966 was partially reversed by anti-IL-10 treatment.

Figure 7:
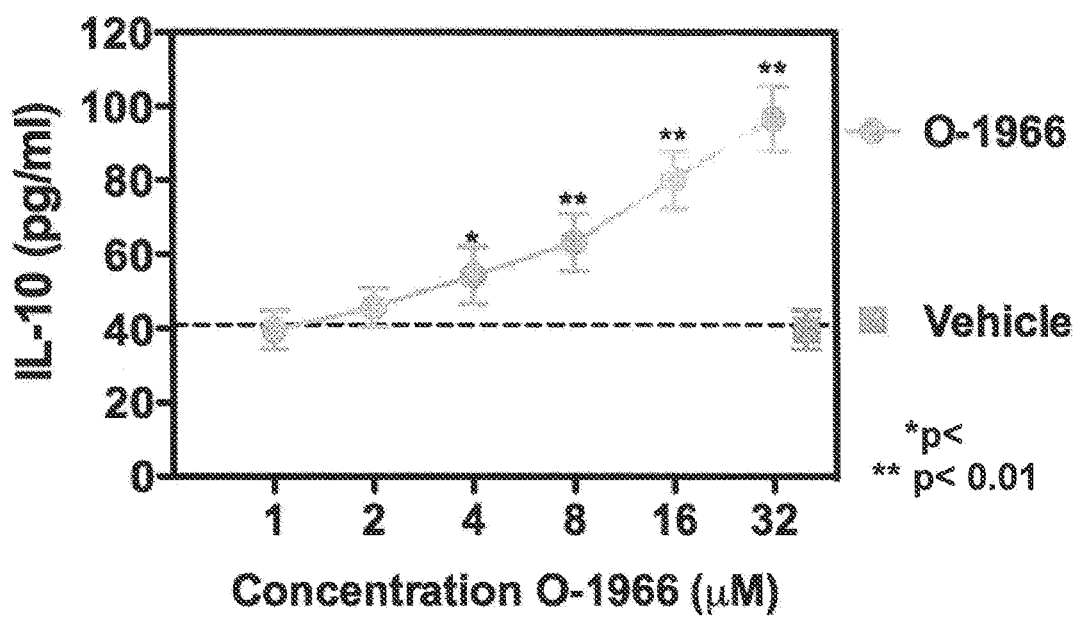
FIG. 7 is a graph showing that O-1966 increased IL-10 release in the MLR.
Figure 9:
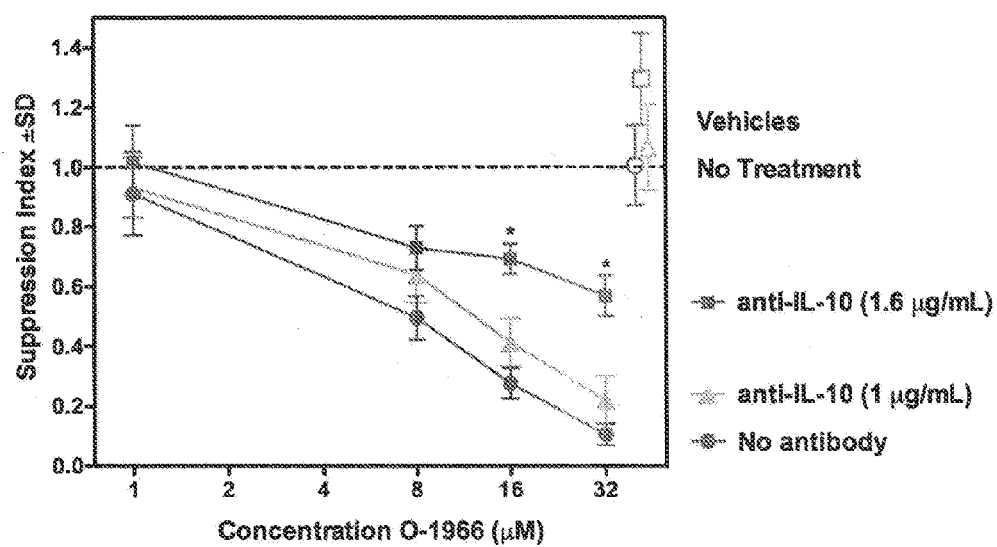
FIG. 9 is a graph showing that suppression of proliferation by O-1966 was partially reversed by anti-IL-10 treatment.

An MLR assay was performed in which experimental wells received 32 μM/ml of O-1966 and control wells received vehicle (FIGS. 7 and 9). Supernatants were collected after 24 hours. Treatment with O-1966 increased IL-10 release in the MLR by 2.46 fold: No treatment: 39.38 μg/ml, vehicle: 39.69 pg/ml, O-1966 at 32 μM: 96.75 pg/ml. IL-10 is an immunosuppressive cytokine, so its rise induced by the $CB_2$ receptor agonist provides a mechanism of action for the cannabinoid in suppressing the MLR. In a separate MLR some wells received 1.6 μg/ml of anti-IL-10 antibody. Wells that received no antibody and 32 μM 0-1966 had 90% suppression of proliferation compared to untreated cells. Cells that were treated with anti-IL-10 antibody and 32 μM O-1966 had 43% suppression of proliferation compared to wells that received anti-IL-10 antibody only.

Example 7

O-1966 treatment doubled the number of Tregs in the MLR.

Figure 8:
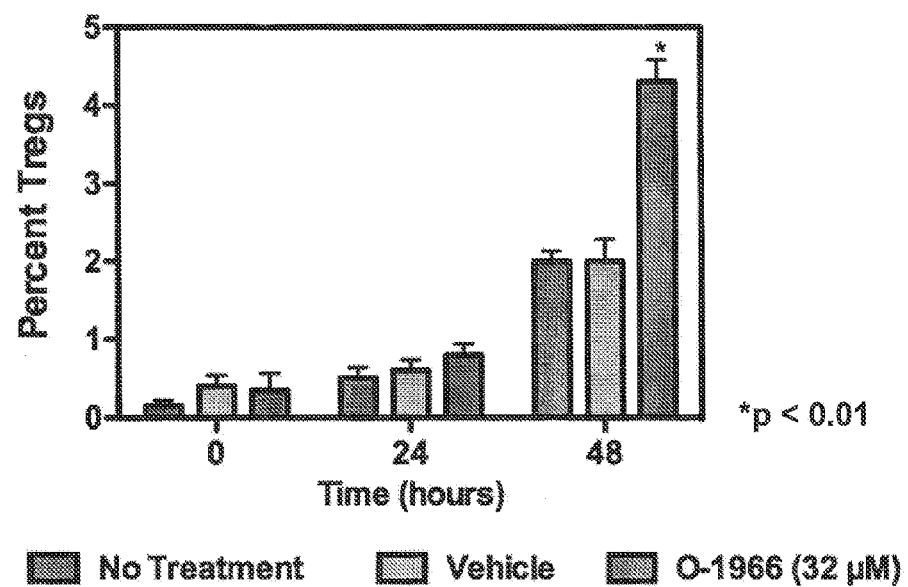
FIG. 8 is a graph showing that O-1966 treatment doubled the number of Tregs in the MLR.

An MLR assay was performed in which experimental wells received 32 μM/ml of O-1966 and control wells received vehicle (FIG. 8). At 48 hours, cells were harvested and stained for expression of Foxp3 and CD4 (Cells that are double positive for these two markers are considered Tregs). Cells were analyzed for marker expression by flow cytometry. Wells that received no treatment had 2.1%+/−0.14 Tregs compared to wells that were treated with 32 μM O-1966 which had 4.3%+/−0.27 Tregs. These differences were statistically significant, as 20,000 cells were counted in each group. Tregs are a relatively newly recognized subset of T-cells that suppress T-cell immune responses. Thus, an increase their number induced by the CB2 receptor agonist provides a second mechanism by which the cannabinoid is altering T-cell responsiveness in the MLR assay.

Example 8

Anti-IL-10 antibody treatment partially blocked the increase in Tregs induced by O-1966 in the MLR.

Figure 10:
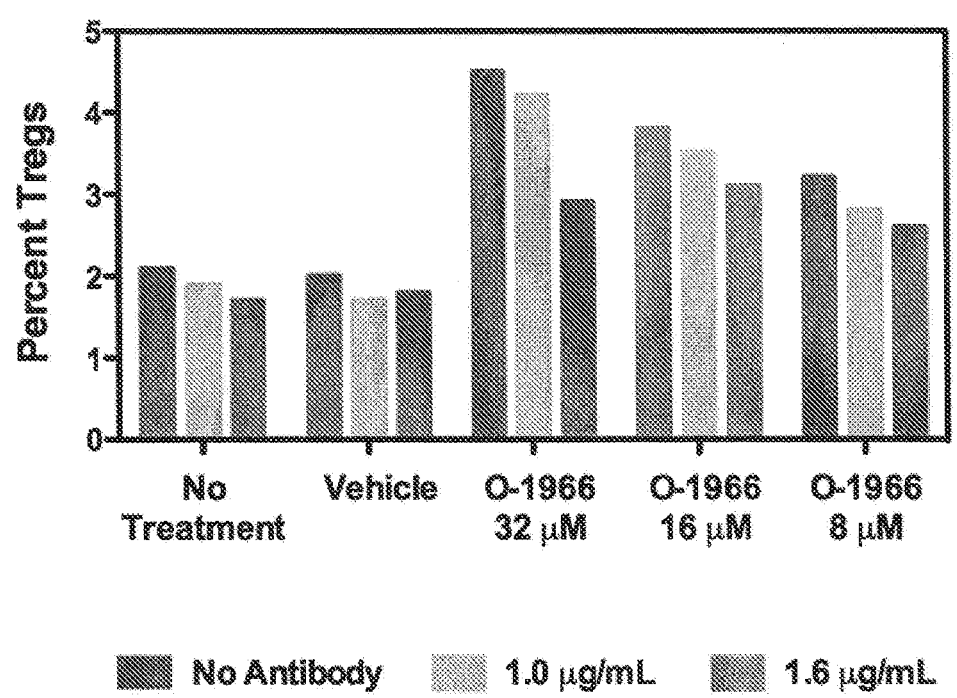
FIG. 10 is a graph showing that anti-IL-10 antibody treatment partially blocked the increase in Tregs induced by O-1966 in the MLR.

An MLR was performed in which some wells received 1.6 μg/ml of anti-IL-10 antibody (FIG. 10). Cells were harvested at 48 hours and stained as described under #3 above for Tregs. Cells that received 32 μM O-1966 and no anti-IL-10 antibody had 4.3%+/−0.28 Tregs. Wells that received only anti-IL-10 antibody and no O-1966, had 1.7%+/−0.16 Tregs. Wells that received anti-IL-10 antibody in addition to 32 μM O-1966 had 2.9%+/−0.25 Tregs. Thus, anti-IL10 treatment partially blocked the increase in Tregs induced by the cannabinoid.

Example 9

In vivo studies on effects of a selective $CB_2$ receptor agonist on skin graft rejection in mice.

Figure 11:
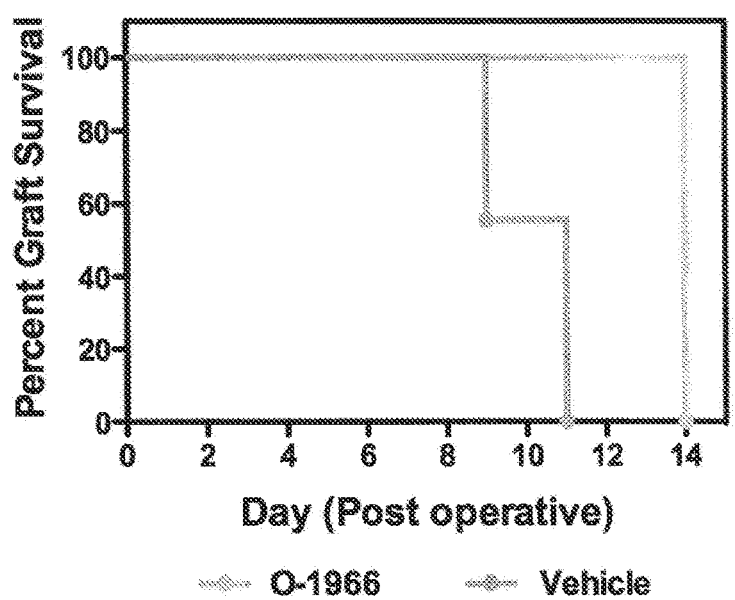
FIG. 11 is a graph showing that O-1966 prolonged skin graft rejection in mice.

Groups of C57Bl/6 mice received skin grafts from C3HeB/FeJ mice that are histoincompatible (FIG. 11). Starting one hour before grafting mice were treated by intraperitoneal injection with either 5 mg/kg of the CB2 receptor agonist, O-1966, or vehicle. (Volumes were based on weight. but were usually approximately 0.2 ml.) every other day for 14 days, and monitored for graft rejection. Mice that received O-1966 treatment had viable grafts 2.7 days longer than vehicle treated mice, which was statistically significant.

Example 10

Ex vivo studies on effects of a selective $CB_2$ receptor agonist administered in vivo to mice receiving skin grafts.

Figure 12:
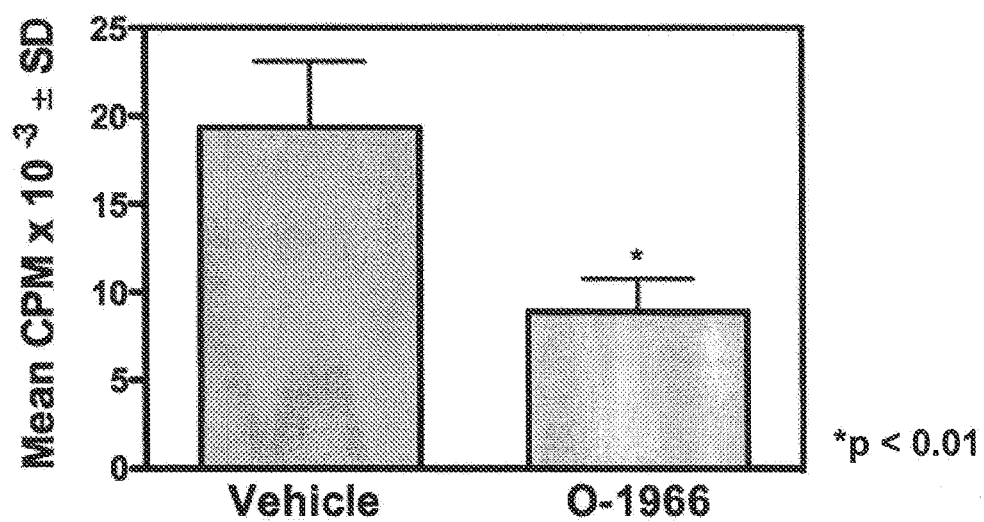
FIG. 12 is a graph showing that splenocytes from O-1966 treated skin graft recipient mice had decreased proliferation in an ex vivo MLR.

Splenocytes from O-1966 treated skin graft recipient mice have decreased proliferation in an ex vivo MLR. (FIG. 12). Groups of mice received skin grafts and were treated with either 5 mg/kg O-1966 or vehicle every other day for 14 days. Spleens were removed on day 14 and placed in an MLR assay. The cells were restimulated in vitro with splenocytes from an incompatible mouse strain, but they received no additional treatment with a cannabinoid in vitro. It was found that cells harvested from O-1966 treated mice exhibited 50% decreased proliferation after 48 hr in culture compared to cells harvested from vehicle treated mice.

Figure 13:
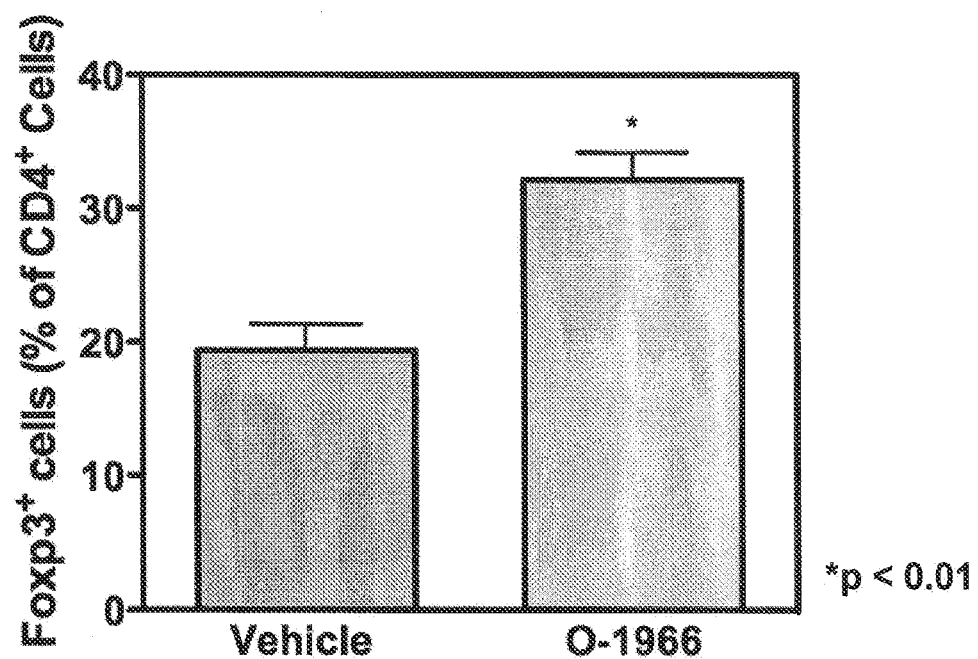
FIG. 13 is a graph showing that O-1966 treated mice that received skin grafts had an increased percentage of splenic Tregs.
Figure 14:
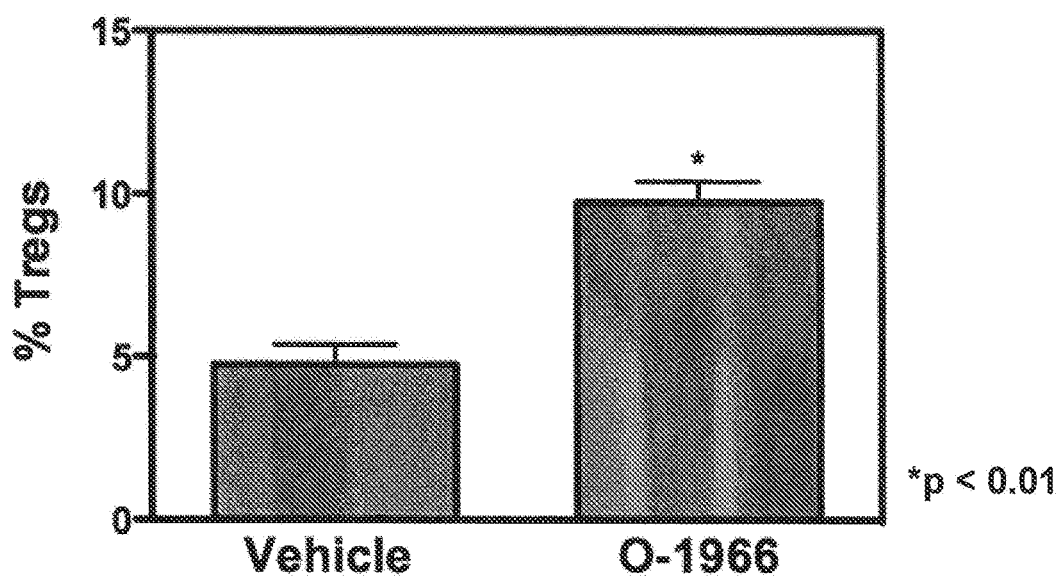
FIG. 14 is a graph showing that splenocytes from O-1966 treated mice that received skin grafts had an increased percentage of Tregs after ex vivo MLR.

O-1966 treated mice that received skin grafts have an increased percentage of splenic Tregs. (FIGS. 13 and 14): Spleen cells taken from the animals described in C1 above were harvested from animals, and a sample was immediately analyzed by flow cytometry. Another sample was placed in culture for 48 hours. It was found that in cell samples that were analyzed immediately after sacrifice of the mice the Tregs (CD4+, Foxp3') in vehicle treated mice constituted 19.4% of the CD4 cells, as compared to 32.2% in the cells from the O-1966 treated mice. Cells that were harvested after 48 hours in the MLR had 4.75% Tregs in the vehicle treated mice and 9.7% Tregs in the O-1966 treated mice.

Figure 15:
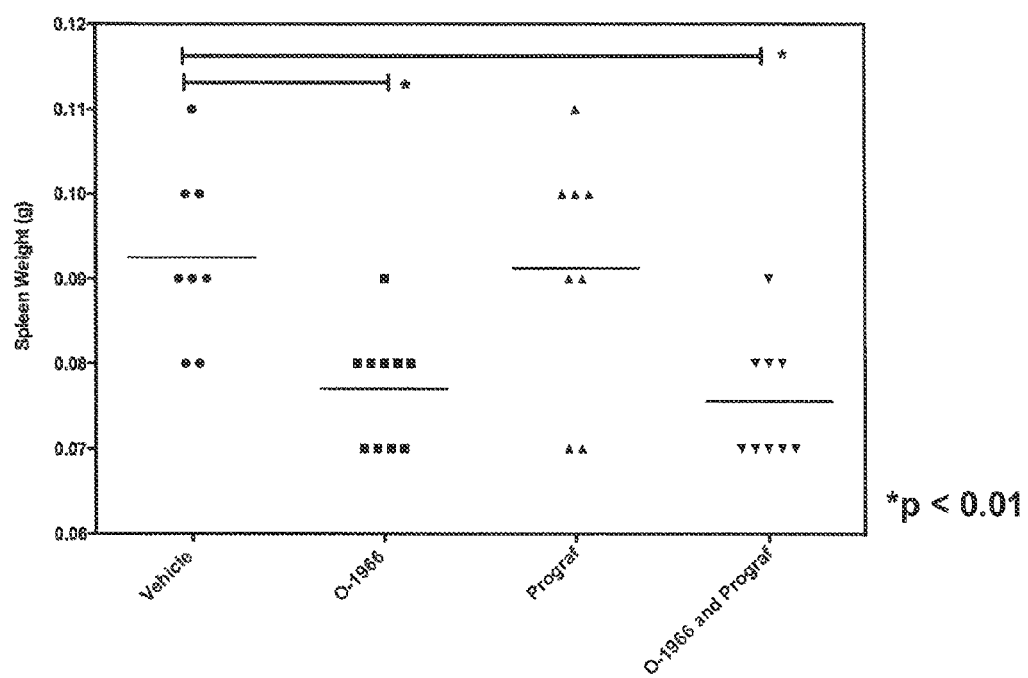
FIG. 15 is a graph showing that O-1966 treated mice that received skin grafts had decreased spleen weights.
Figure 16:
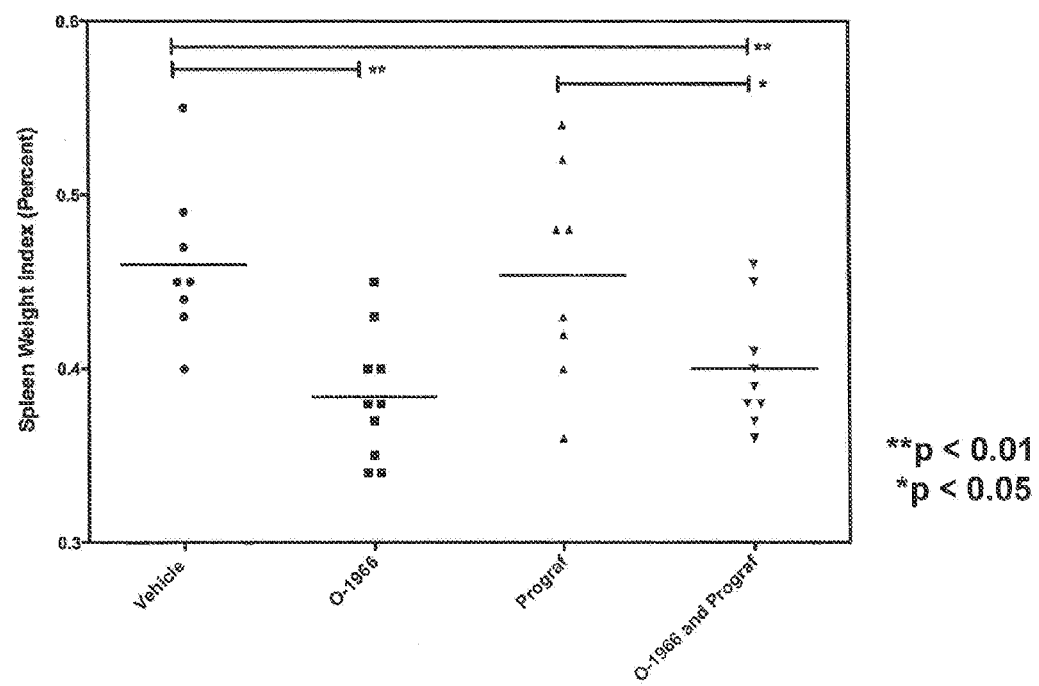
FIG. 16 is a graph showing that O-1966 treated mice that received skin grafts had decreased splenic indices.

O-1966 treated mice that received skin grafts have decreased spleen weights. FIGS. 15 and 16.

Spleens were removed on Day 14 and weighed. Spleens from vehicle treated mice were 0.093+/−0.01 grams and spleens from O-1966 mice were 0.077+/−0.006 grams. Spleens of untreated mice average 0.072+/−0.009 grams (historical data). The average spleen weight index ([spleen weight/body weight]×100) was 0.46% in vehicle treated mice and 0.38% in O-1966 treated mice.

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

Those of skill in the art, in light of the present disclosure, will appreciate that obvious modifications of the embodiments disclosed herein can be made without departing from the spirit and scope of the invention. All of the embodiments disclosed herein can be made and executed without undue experimentation in light of the present disclosure. The full scope of the invention is set out in the disclosure and equivalent embodiments thereof. The specification should not be construed to unduly narrow the full scope of protection to which the present invention is entitled.

While a particular embodiment of the invention has been shown and described, numerous variations and alternate embodiments will occur to those skilled in the art. Accordingly, it is intended that the invention be limited only in terms of the appended claims.

The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes to the claims that come within the meaning and range of equivalency of the claims are to be embraced within their scope.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A method of reducing the likelihood of graft rejection in a patient in need thereof comprising the administration of a therapeutically effective amount of a selective $CB_2$ receptor agonist, wherein the selective $CB_2$ receptor agonist is set forth as Formula I:

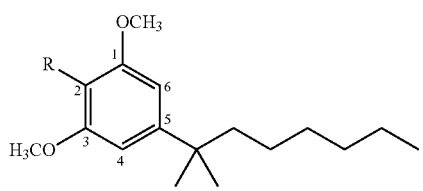

Formula I wherein R is a cycloalkyl or thiocycloalkyl optionally substituted with C1-3 alkyl or hydroxyalkyl.

2. The method of claim 1, further comprising administration of a therapeutically effective amount of an immunosuppressive agent, a $CB_1$ receptor antagonist or a combination thereof.

3. The method of claim 1, wherein the graft is an allograft or a xenograft.

4. The method of claim 1, wherein the graft is an organ graft.

5. The method of claim 4, wherein the organ is or comprises a heart, kidney, liver or a lobe thereof, lung or a lobe thereof, pancreas or a portion thereof, bone marrow, cartilage, skin, a cornea, neuronal tissue, or muscle.

6. The method of claim 3, wherein the graft comprises a population of cells that do not define an intact organ.

* * * * *

UNITED STATES PATENT AND TRADEMARK OFFICE
CERTIFICATE OF CORRECTION

| | |
|---|---|
| PATENT NO. | : 9,855,225 B2 |
| APPLICATION NO. | : 14/239413 |
| DATED | : January 2, 2018 |
| INVENTOR(S) | : Toby K. Eisenstein et al. |

It is certified that error appears in the above-identified patent and that said Letters Patent is hereby corrected as shown below:

In the Specification

Column 1, paragraph 2, under U.S. GOVERNMENT RIGHTS, the language should be changed from: "This invention was supported in part by United States Government Grant No. DA13429, DA06650 and T32-DA07237 awarded by National Institutes of Drug Abuse. The United States Government may have certain rights in the invention."

To:
--This invention was made with government support under DA006650, DA007237, and DA013429 awarded by the National Institutes of Health. The government has certain rights in the invention.--

Signed and Sealed this
Fourteenth Day of November, 2023

Katherine Kelly Vidal
*Director of the United States Patent and Trademark Office*